(12) United States Patent
Thornton et al.

(10) Patent No.: US 10,028,662 B2
(45) Date of Patent: Jul. 24, 2018

(54) SYSTEMS AND METHODS FOR IMAGING BIOLOGICAL TISSUE STRUCTURES

(71) Applicant: ENDRA, INC., Ann Arbor, MI (US)

(72) Inventors: Michael M. Thornton, London (CA); Paul A. Picot, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 97 days.

(21) Appl. No.: 14/712,214

(22) Filed: May 14, 2015

(65) Prior Publication Data

US 2017/0311808 A1    Nov. 2, 2017

(51) Int. Cl.
     *A61B 5/00*      (2006.01)
     *A61B 8/14*      (2006.01)
     (Continued)

(52) U.S. Cl.
     CPC .......... *A61B 5/0093* (2013.01); *A61B 5/0035* (2013.01); *A61B 8/145* (2013.01);
     (Continued)

(58) Field of Classification Search
     CPC ..... A61B 5/0035; A61B 8/145; A61B 8/4477; A61B 8/4494; A61B 8/5261
     See application file for complete search history.

(56) References Cited

U.S. PATENT DOCUMENTS 4,246,784 A    1/1981   Bowen
4,385,634 A    5/1983   Bowen
(Continued)

FOREIGN PATENT DOCUMENTS

JP    WO 2009154298 A1 * 12/2009 ........... A61B 5/0095

OTHER PUBLICATIONS

Jeong. "Dual-concentric LiNbO3/P(VDF-TrFE) Copolymer Transducer for High-frequency Ultrasound Imaging". Journal of the Korean PHysical Society, 2013, vol. 63, No. 5, pp. 986-990.*
(Continued)

*Primary Examiner* — Katherine Fernandez
*Assistant Examiner* — Yi-Shan Yang
(74) *Attorney, Agent, or Firm* — Tarolli, Sundheim, Covell & Tummino LLP

(57) ABSTRACT

A thermoacoustic imaging system is provided for use in combination with an ultrasound imaging system for imaging features of tissue, the ultrasound imaging system including an ultrasound imaging probe including a transmit-receive transducer array with a plurality of transmit-receive array elements. The thermoacoustic imaging system includes a receive-only transducer array with a plurality of receive-only array elements, registered with the plurality of transmit-receive array elements. The transmit-receive transducer array is housed in an ultrasound imaging probe, and the receive-only transducer array is housed in a thermoacoustic imaging probe. The thermoacoustic imaging probe is mechanically joined to the ultrasound imaging probe, e.g., as a sleeve fitted to the ultrasound imaging probe. A combined ultrasound transducer system including the ultrasound imaging probe and an thermoacoustic imaging probe may be used in composite imaging of tissue based upon the registration of the receive-only array elements with the transmit-receive array elements.

13 Claims, 16 Drawing Sheets

(51) Int. Cl.
  *A61B 8/00* (2006.01)
  *A61B 8/08* (2006.01)
(52) U.S. Cl.
  CPC .............. *A61B 8/42* (2013.01); *A61B 8/4477* (2013.01); *A61B 8/4494* (2013.01); *A61B 8/5261* (2013.01)

(56) References Cited

U.S. PATENT DOCUMENTS

| | | |
|---|---|---|
| 5,713,356 A | 2/1998 | Kruger |
| 5,840,023 A | 11/1998 | Oraevsky et al. |
| 2011/0301467 A1* | 12/2011 | Miller .................. A61B 8/4477 600/459 |
| 2011/0306865 A1 | 12/2011 | Thornton et al. |
| 2012/0197117 A1 | 8/2012 | Picot et al. |
| 2014/0018660 A1* | 1/2014 | Wada .................... A61B 8/4411 600/407 |
| 2015/0032002 A1* | 1/2015 | Rothberg ............ G01S 7/52084 600/440 |
| 2015/0112181 A1* | 4/2015 | Yoon .................... A61B 5/0095 600/407 |

OTHER PUBLICATIONS

Kolkman, R. G. M., et al., "Real-time in vivo photoacoustic and ultrasound imaging," Journal of Biomedical Optics, vol. 13(5), Sep./Oct. 2008, pp. 050510-1-050510-3.

Vaithilingam, S., et al., "Capacitive Micromachined Ultrasonic Transducers (CMUTs) for Photoacoustic Imaging," Proc. of SPIE, vol. 6086, 2006, pp. 608603-1-608603-11.

Wang, Y., et al., "In vivo three-dimensional photoacoustic imaging based on clinical matrix array ultrasound probe," Journal of Biomedical Optics, vol. 17(6), Jun. 2012, pp. 061208-1-061208-5.

* cited by examiner

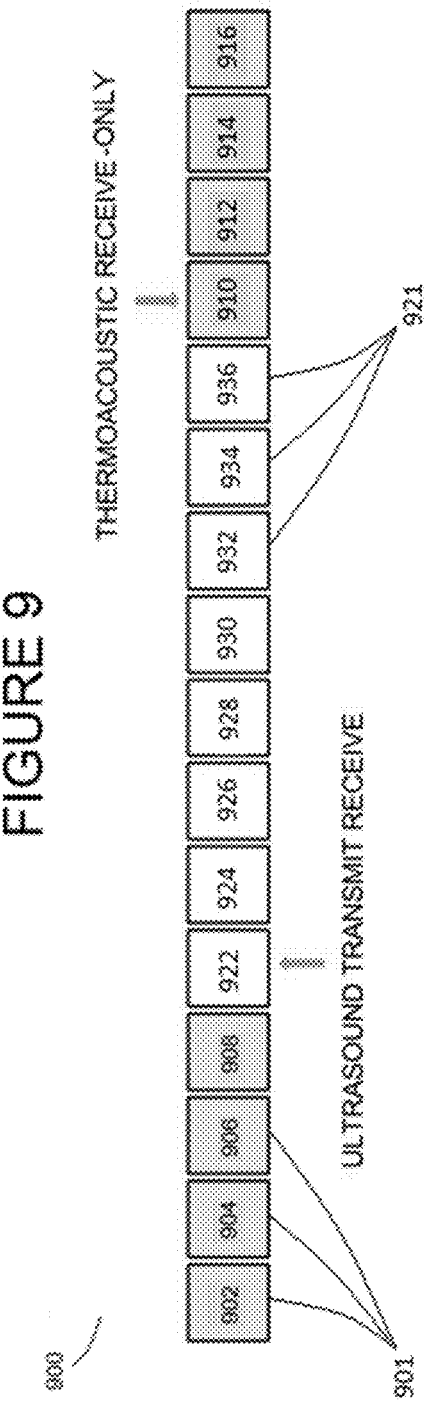

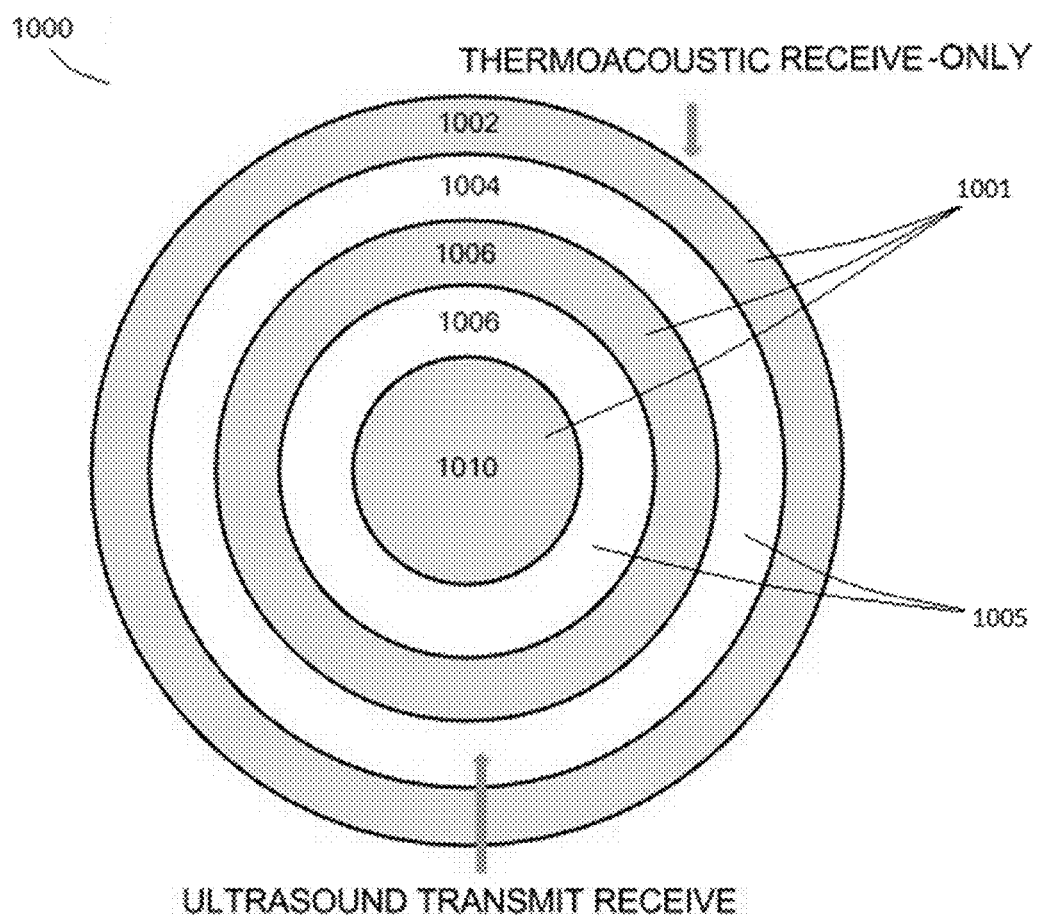

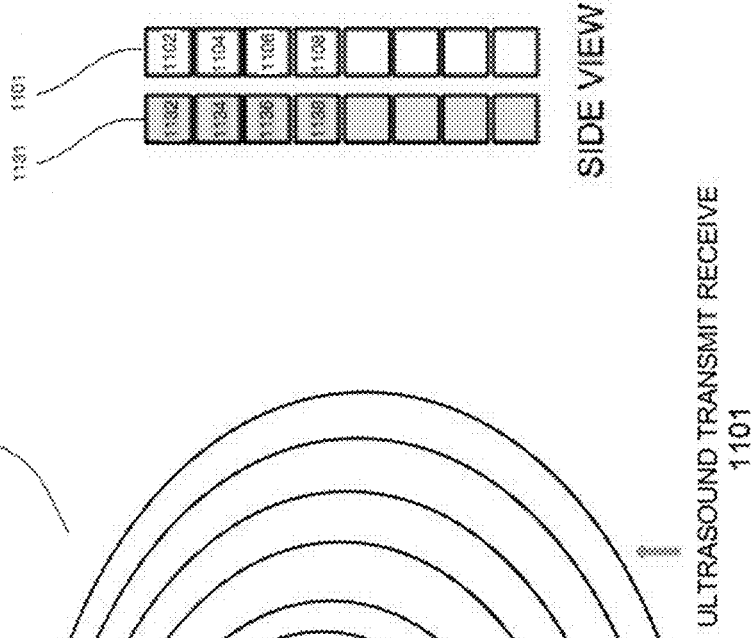
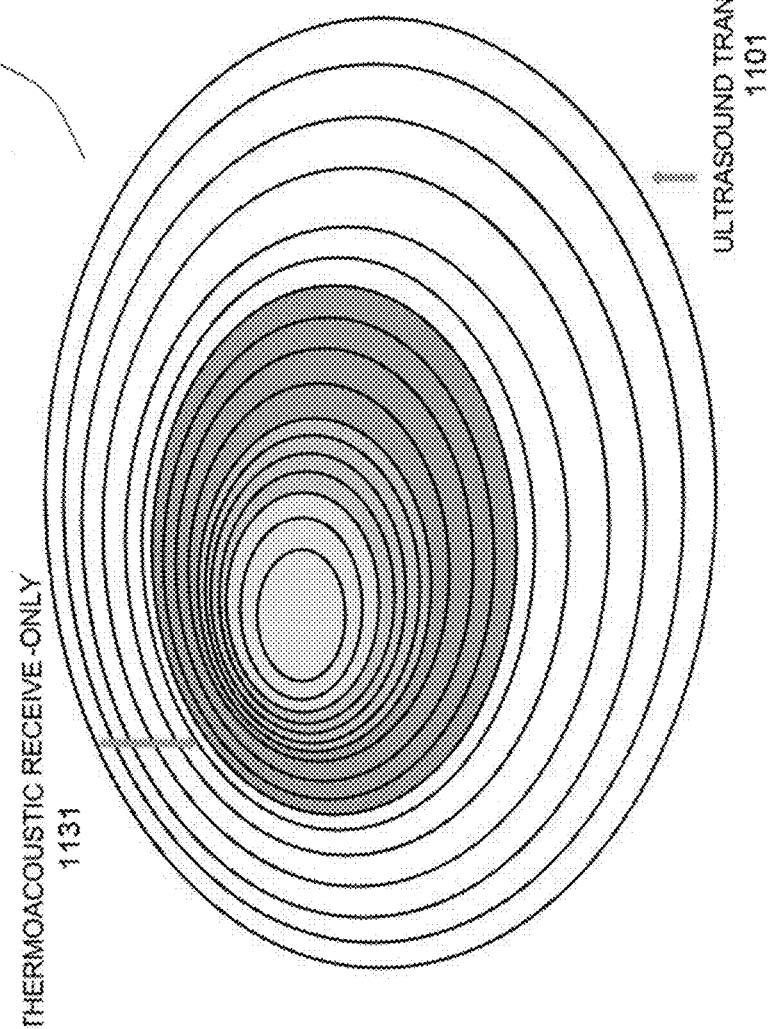

AREA DETECTOR

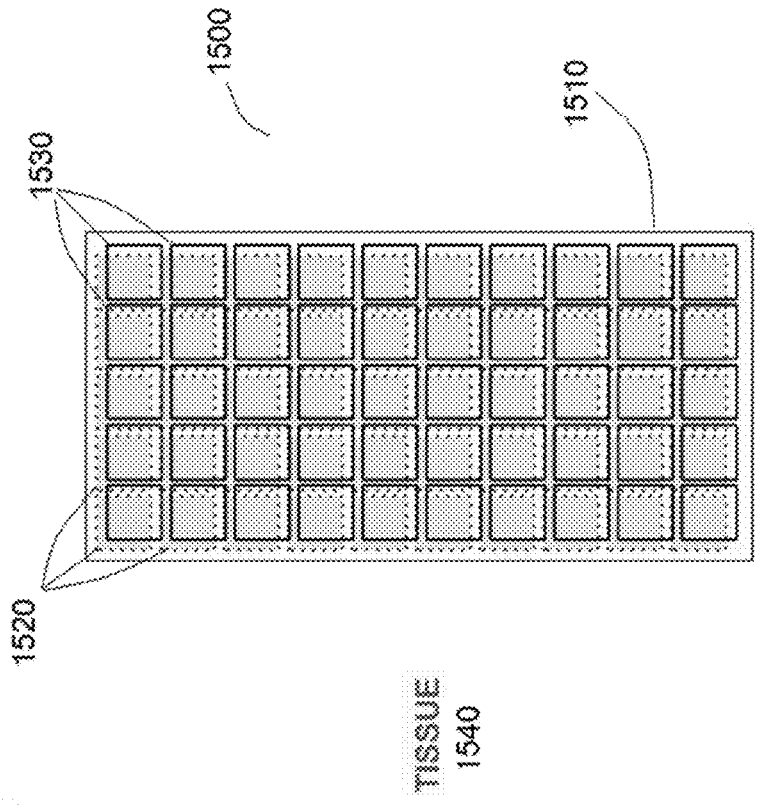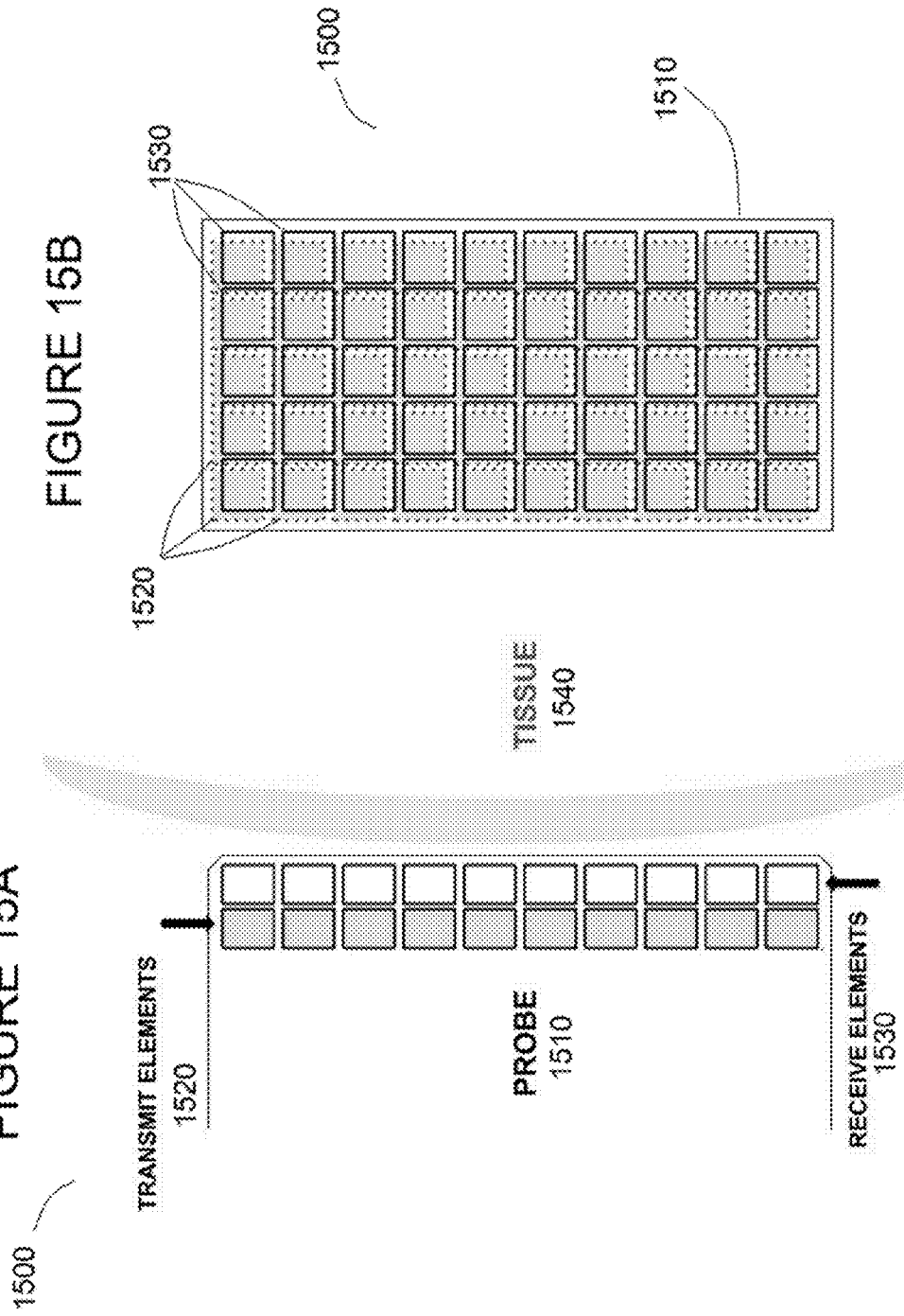

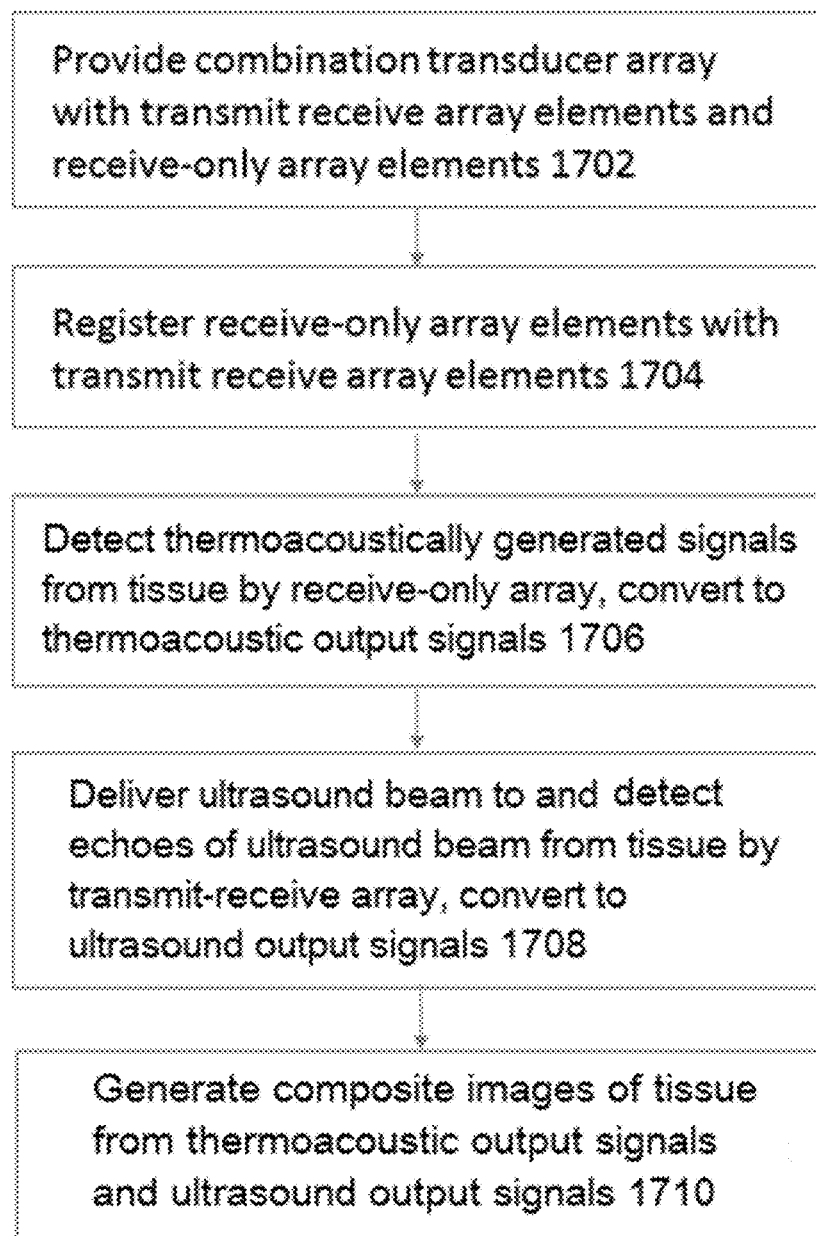

SYSTEMS AND METHODS FOR IMAGING BIOLOGICAL TISSUE STRUCTURES

TECHNICAL FIELD

The present disclosure relates to imaging structures and properties of tissue using ultrasound and thermoacoustic techniques.

BACKGROUND

In traditional ultrasound medical imaging, or sonography, a single array of ultrasound transducers (herein sometimes called a transmit-receive array) operates both to transmit and receive ultrasound energy. Ultrasound transducer elements transmit ultrasound waves into an object (e.g., tissue). The transmitted energy is scattered and reflected by the tissue, and the scattered and reflected ultrasound energy is received by the same ultrasound transducer elements. The ultrasound transducer converts received ultrasound energy to electrical signals. The received ultrasound signals are analyzed and interpreted through signal processing, generally providing information on location of structures within the tissue.

In medical ultrasound imaging, ultrasound pulses are used in a manner similar to radar, where a pulse is transmitted, and then echoes are received from reflections and from scatter within tissue. In radar (RAdio Detection And Ranging), a short pulse of an electromagnetic (radiofrequency or microwave) carrier wave is transmitted, and echoes or reflections are detected by a receiver, typically co-located with the transmitter. The range of radar is limited by the received signal energy. Analogously, in ultrasound medical imaging, strong, short electrical pulses transmitted by the ultrasound system drive the transducer at a desired frequency in order to achieve good range resolution. The two-way time of flight of received echoes yields range information, and the strength of the received echoes provides information on acoustical impedance (e.g., when a transmitted pulse encounters a structure within tissue with a different density, and reflects back to the transducer). With knowledge of the direction of the transmitted pulse, an ultrasound image, or sonogram, is created. In ultrasound medical imaging, the maximum transmitted power is limited by the voltage tolerated in the system electronic components, and by the peak intensity permitted by safety considerations pertaining to tissue exposure. As in radar, the range is limited by the received signal versus background noise, which is in turn limited by total pulse energy.

Thermoacoustic imaging, sometimes called photoacoustic or optoacoustic imaging, is a technology used in characterizing and imaging materials based on their electromagnetic and thermal properties, having applications in nondestructive testing, clinical diagnostics, medical imaging, life sciences and microscopy. Thermoacoustic imaging uses short pulses of electromagnetic (EM) energy, i.e., the excitation energy, to rapidly heat features within an object that absorb the EM energy (excitation sites). This rapid heating causes the material (e.g., tissue) to increase in pressure slightly, inducing acoustic pulses that radiate from the excitation site as an ultrasound wave. These acoustic pulses are detected using acoustic receivers, such as an array of ultrasound transducers, located at the material's surface. The resulting measurements are analyzed and interpreted through signal processing using time-of-flight and related algorithms, which reconstruct the distribution of absorbed EM energy, sometimes called thermoacoustic computed tomography (TCAT). The result can be displayed to the user as depth profile plots, or as 2-, 3-, or 4-dimensional images.

There are different requirements for clinical ultrasound transducers operating in transmit-receive mode versus receive-only ultrasound transducers employed in thermoacoustic imaging. Clinical ultrasound transducer arrays are constructed and optimized to operate in both transmit and receive ultrasound modes. These ultrasound transducers require high operating efficiency in transmitting and receiving ultrasound energy, which is not a requirement of receive-only transmitters used in thermoacoustic imaging. Clinical ultrasound transducers typically use a lens to provide an optimal depth of focus, and are designed with an optimized frequency of operation. Traditional ultrasound imaging relies upon narrow band reception for image resolution.

By contrast, in thermoacoustic imaging, it is important for the receive-only transducers to receive and process a wide band of frequencies. Thermoacoustic transducer elements and arrays are designed to operate with a high sensitivity in receive-only mode, whereas receive-only transducers do not have to meet the transmission efficiency requirements of transmit-receive elements and arrays. Thermoacoustic image resolution is determined by frequency of the acoustic signal. This frequency in determined by characteristics of the material being imaged, not by the frequency of the emitted electromagnetic energy ("EM", or excitation, energy). To be able to discriminate a range of materials properties in thermoacoustic imaging (e.g., small and large size structures; imaging shallow materials and deep materials), wide reception bandwidth is critical. A reception bandwidth on the order of 3-6 MHz is considered a fairly wide range, and higher bandwidths are desirable.

One consideration in image formation in both ultrasound imaging and in thermoacoustic imaging is transducer geometry, e.g., geometry of transducer arrays. Different transducer geometries, such as single focused transducer, linear arrays, and two-dimensional arrays, are capable of different modes of image formation. Depending in part on the transducer geometry, the imaging system may for example image single lines, two-dimensional regions, or three-dimensional volumes. The imaging operation also may employ scanning, or motion of the transducers or transducer arrays, to adapt transducer operation to different modes of imaging.

Traditional clinical ultrasound technology indicates locations of features within a tissue or other material, but provides no functional characteristics. On the other hand, thermoacoustic imaging combines absorption contrasts achieved through interaction of the imaged material with the EM excitation energy, with fine ultrasound resolutions characteristic of acoustic reception, thereby enabling deep penetration in in vivo imaging. Thermoacoustic technology can detect dynamic features, and can measure various functional characteristics of anatomy.

SUMMARY

It is known to combine clinical ultrasound transducers and thermoacoustic transducers in a single system for imaging tissue features, but conventional tissue imaging systems do not use each of these technologies with the transducers and related components configured to operate most effectively in both types of imaging. Nor do conventional tissue imaging systems provide effective composite images including the location information characteristic of traditional ultrasound technology with dynamic and functional characteristics that can be provided by thermoacoustic technology. For the foregoing reasons, there is a need for a system and method that employs ultrasound imaging technology in combination with thermoacoustic imaging technology in effective and versatile composite imaging of tissue features.

The embodiments described herein include a combined ultrasound transducer system for imaging tissue, including first and second transducer arrays. A first transducer array is configured for transmit-receive ultrasound imaging. The second transducer array system is configured for thermoacoustic receive-only imaging. In one embodiment, the present disclosure provides an ultrasound system for imaging structures of tissue, including a combined ultrasound transducer array coupled to the tissue. In another embodiment, the present disclosure provides a thermoacoustic imaging system that is designed to be added to the existing ultrasound imaging system to provide a combined ultrasound transducer array. In both embodiments, the combined ultrasound transducer array includes a transmit-receive transducer array having a plurality of transmit-receive array elements, and a receive-only transducer array having a plurality of receive-only array elements. The receive-only array elements are registered with the transmit-receive array elements.

In an embodiment, a transducer for imaging structures of tissue, comprises a transmit-receive transducer array including a plurality of transmit-receive array elements, wherein the transmit-receive transducer array receives and detects echoes from an ultrasound beam delivered into the tissue by the transmit-receive transducer array, and converts the echoes to ultrasound output signals, and a receive-only transducer array including a plurality of receive-only array elements, wherein the receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals, wherein the receive-only array elements are registered with the transmit-receive array elements in the transducer.

In an embodiment, an imaging system for imaging structures of tissue, comprises an ultrasound probe including a transmit-receive transducer array comprising a plurality of transmit-receive array elements, and a receive-only transducer array comprising a plurality of receive-only array elements, wherein the receive-only array elements are in registration with and surround the transmit receive array elements within the ultrasound probe; wherein the receive-only transducer array receives and detects thermoacoustically-generated acoustic signals in response to electromagnetic energy delivered into the tissue by a source of electromagnetic energy and detected by the receive-only transducer array, and converts the thermoacoustically-generated acoustic signals to thermoacoustic output signals; and wherein the transmit-receive transducer array receives and detects echoes from an ultrasound beam delivered into the tissue by the transmit-receive transducer array, and converts the echoes to ultrasound output signals; and an imaging assembly for processing the thermoacoustic output signals and the ultrasound output signals to generate images of the structures of tissue.

In another embodiment, a method for operating an ultrasound imaging system to image features of tissue, comprises transmitting, by transmit-receive array elements of a transmit-receive transducer array, an ultrasound beam to the tissue from the transmit-receive transducer array of combined transducer arrays, the combination transducer array having the transmit-receive transducer array and a receive-only transducer array, wherein receive-only array elements of the receive-only transducer array are registered with the transmit-receive array elements of the transmit-receive transducer array; receiving, by the receive-only array elements, thermoacoustically-generated acoustic signals generated within the tissue in response to electromagnetic energy delivered to the tissue and converting the thermoacoustically-generated acoustic signals to thermoacoustic output signals; receiving, by the transmit-receive array elements, echoes of the ultrasound beam transmitted to the tissue and converting the echoes to ultrasound output signals; and generating, by the ultrasound imaging system, a composite image of the tissue from the thermoacoustic output signals and the ultrasound output signals.

In another embodiment, a transducer for imaging structures of tissue comprises a transmit-receive transducer array including a plurality of transmit-receive array elements, wherein the transmit-receive transducer array has a first mode of operation in which it is configured to receive and detect echoes from an ultrasound beam delivered into the tissue by the transmit-receive transducer array and convert the echoes to ultrasound output signals, and a second mode of operation in which it is configured to receive and detect thermoacoustically generated acoustic signals in response to electromagnetic energy delivered into the tissue by a source of electromagnetic energy, and convert the thermoacoustically generated acoustic signals to thermoacoustic output signals; and a receive-only transducer array including a plurality of receive-only array elements, wherein the receive-only transducer array is configured to receive and detect acoustic signals that are thermoacoustically generated in response to the electromagnetic energy delivered into the tissue by the source of electromagnetic energy, and convert the acoustic signals that are thermoacoustically generated to thermoacoustic output signals.

In a further embodiment, a thermoacoustic imaging system for use in combination with an ultrasound imaging system for imaging features of tissue, the ultrasound imaging system including a transmit-receive transducer array, wherein the transmit-receive transducer array receives and detects echoes from an ultrasound beam delivered into the tissue by the transmit-receive transducer array, and converts the echoes to ultrasound output signals, the thermoacoustic imaging system comprises a source of electromagnetic energy; and a receive-only transducer array including a plurality of receive-only array elements, wherein the receive-only array elements are registered with the transmit-receive transducer array, wherein the receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals.

In yet another embodiment, a thermoacoustic imaging probe is provided for use in combination with an ultrasound imaging system for imaging features of tissue, the ultrasound imaging system including a transmit-receive transducer array that receives and detects echoes from an ultrasound beam delivered into the tissue by the transmit-receive transducer array and that converts the echoes to ultrasound output signals, and an ultrasound imaging probe that houses the transmit-receive transducer array; wherein the thermoacoustic imaging probe comprises a receive-only transducer array including a plurality of receive-only array elements housed in the thermoacoustic imaging probe, wherein the receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals; and wherein the plurality of receive-only array elements housed in the thermoacoustic imaging probe are registered with the plurality of transmit-receive array elements housed in the ultrasound imaging probe.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 9 illustrates a combination transducer array, according to an exemplary embodiment.

FIG. 10 illustrates a combination transducer array, according to an exemplary embodiment.

FIG. 11A is a perspective view of a combination transducer array, according to an exemplary embodiment.

FIG. 11B is a side view of the combination transducer array of FIG. 11A.

FIG. 15A is a side view of an ultrasound probe including a combination transducer array disposed for imaging tissue, according to an exemplary embodiment.

FIG. 15B is a front plan view of the ultrasound probe with combination transducer array of FIG. 15A.

FIG. 17 illustrates steps of operating an ultrasound imaging system to image features of tissue, according to an exemplary embodiment.

DETAILED DESCRIPTION

Figure 1:
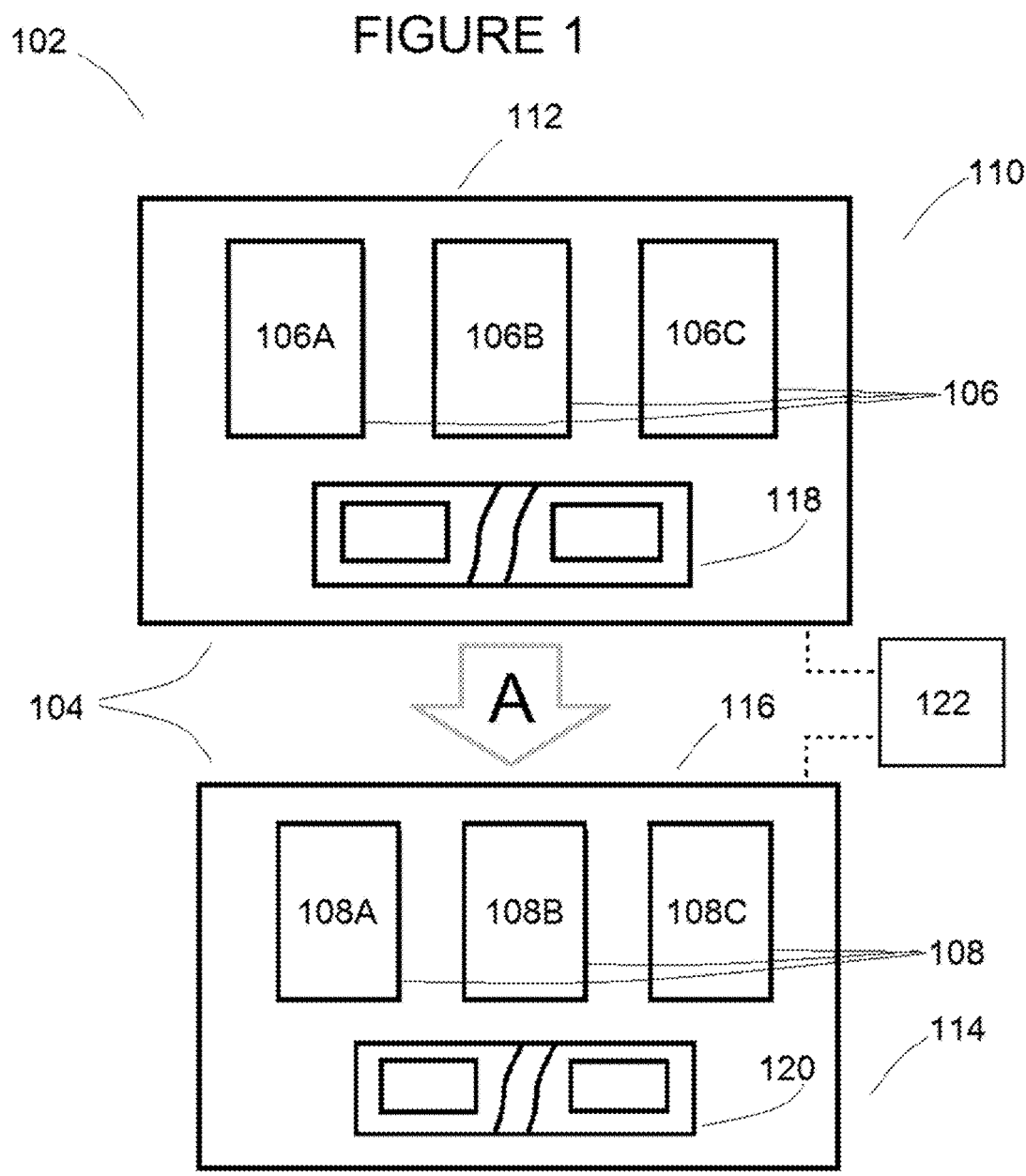
FIG. 1 illustrates a system overview of an imaging system including a combination transducer array, according to an exemplary embodiment.

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here. Furthermore, the various components and embodiments described herein may be combined to form additional embodiments not expressly described, without departing from the spirit or scope of the invention.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

The present disclosure describes a combined ultrasound transducer system including first and second arrays of transducer elements (also herein called transducer arrays). A first transducer array is configured for transmit-receive ultrasound imaging. The second transducer array is configured for thermoacoustic receive-only imaging. The first transducer array may be referred to herein as a transmit-receive array, transmit-receive transducer, or transmit-receive transducer array. The second transducer array may be referred to herein as a receive-only (or receive) array, receive-only transducer, or receive-only transducer array.

In an embodiment, a "transducer" as used in the present disclosure can represent a component that converts pressure waves to another form of energy, typically as part of a system for ultrasound imaging, thermoacoustic imaging, or both types of imaging. In one embodiment, the transducer converts pressure to electrical energy. In other embodiments, the transducer converts pressure to other forms of energy such as optical energy or mechanical energy. Output signals of the transducer, when operating in thermoacoustic imaging, are sometimes herein called "thermoacoustic output signals". Output signals of the transducer, when operating in ultrasound imaging, are sometimes herein called "ultrasound output signals". In another embodiment, for a transducer in "transmit" operation, the transducer converts electrical energy or other energy to ultrasound pressure waves.

As used in the present disclosure, an "element" (also herein called "transducer element" or "array element") can represent an individual physical region of a transducer that is capable of emitting or detecting acoustic pressure, or both emitting and detecting acoustic pressure, independently of other elements of the transducer. Typically, elements are non-contiguous regions of the transducer.

As used in the present disclosure, an "array" (also herein called "transducer array") can represent a plurality of transducer elements. In one embodiment, an transducer array includes a regular arrangement of transducer elements.

In one embodiment, an imaging system for imaging structures of tissue includes a transducer array configured for transmit-receive ultrasound imaging, and a transducer array configured for receive-only thermoacoustic imaging. The transmit-receive transducer array includes a plurality of transmit-receive array elements, and the receive-only transducer array includes a plurality of receive-only array elements. The receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals. The transmit-receive transducer array receives and detects echoes from an ultrasound beam delivered into the tissue by the transmit-receive transducer array, and converts the echoes to ultrasound output signals.

In an embodiment, the transmit-receive transducer array and receive-only transducer array are housed in a single ultrasound probe, wherein the receive-only array elements are registered with the transmit-receive array elements within the ultrasound probe. In one embodiment, the receive-only transducer array surrounds the transmit-receive transducer array within the ultrasound probe.

In an embodiment, the imaging system includes an imaging assembly for processing the thermoacoustic output signals and the ultrasound output signals to generate composite images of the structures of tissue. As described below, the registration of the receive-only array elements with the transmit-receive array elements in the imaging system provides various operating advantages in composite imaging.

In another embodiment, a thermoacoustic imaging system is designed for use with an existing or conventional ultrasound imaging system for imaging structures of tissue. The existing ultrasound imaging system includes a transmit-receive transducer array in a first ultrasound probe. The transmit-receive transducer array receives and detects echoes from an ultrasound beam delivered into the tissue by the transmit-receive transducer array, and converts the echoes to ultrasound output signals.

A thermoacoustic imaging system is designed to be added to the existing ultrasound imaging system to provide a combination imaging system. The thermoacoustic imaging system includes a receive-only transducer array with a plurality of receive-only array elements housed in a second ultrasound probe. In an embodiment, the second ultrasound probe takes the form of a sleeve that is joined mechanically to the first ultrasound probe. The thermoacoustic imaging system includes a source of electromagnetic energy, which is delivered into the tissue. The receive-only transducer array receives and detects thermoacoustically-generated acoustic signals generated in response to the electromagnetic energy delivered into the tissue, and converts the thermoacoustically-generated acoustic signals to thermoacoustic output signals. In an embodiment, the combination imaging system includes an imaging assembly that receives the ultrasound output signals and the thermoacoustic output signals to generate composite images of the structures of tissue.

The transmit-receive transducer array and transducer elements comprised in the transmit-receive transducer array are configured for transmit-receive ultrasound imaging. The transmit-receive transducer array, and individual transducer elements included in the transmit-receive transducer array, are configured to transmit and receive ultrasound energy with high operating efficiency. Ultrasound imaging relies on a volume of tissue generating clear, distinctive reflections, scatters, or echoes, of ultrasound energy. Another significant consideration is bandwidth. Ultrasound imaging relies upon narrow band reception for image resolution. Such ultrasound images primarily represent acoustic scattering by small (sub-millimeter) features. A large object, such as an organ, is formed by a collection of many small scatters within the tissue.

The receive-only transducer array and individual transducer elements included in the receive-only transducer array are configured for receive-only ultrasound imaging. Thermoacoustic signals, i.e., pressure waves emitted from absorbers of electromagnetic energy, are very small compared to echoes received in conventional ultrasound imaging. Therefore, the dominant factor in image quality for thermoacoustic imaging is the sensitivity of the transducer. This sensitivity is determined a number of factors, notably including the efficiency with which the acoustic pressure is converted (usually to an electrical signal) by the transducer elements. Often this sensitivity is a function of the thermoacoustic transducer material, as discussed below. Another factor is the area of the transducer element. These factors present certain trade-offs: increasing the area of transducer elements leads to complications in angular response of the transducer elements. With this increase in area, the field of view of the transducer elements decreases, resulting in side-lobes and nulls in the angular response.

Another consideration in configuring transducer arrays, and individual transducer elements included in the arrays, is frequency response (including center frequency and fractional bandwidth). Thermoacoustic images are formed from a plurality of received acoustic frequencies that are related (by the speed of sound in tissue) to the spatial frequencies that form the object. In the case of excitation with RF energy, the bandwidth of a transmitted electromagnetic "excitation" pulse directly affects the frequency content of the thermoacoustic signal emitted by the object, modulated by the spectral frequency content of the object. In practice, an RF pulse has significantly greater bandwidth than the thermoacoustic transducer. The overall sensitivity and degree of artifacts in resulting thermoacoustic images are greatly dependent on the bandwidth of the thermoacoustic transducer. In one embodiment, a receive-only transducer array has an 80% bandwidth based on the frequency of peak sensitivity. For example, a transducer with peak sensitivity of 5 MHz would have 4 MHz bandwidth with FWHM sensitivity from 3 to 7 MHz. An ideal thermoacoustic imaging system would have sensitivity to 0 Hz. In an embodiment, the thermoacoustic transducer has an outstanding sensitivity to 100 kHz.

The selection of transducer materials is another major consideration in configuration of transducer arrays (and configuration of individual transducer elements) as transmit-receive transducers or as receive-only transducers. In general, there is a tradeoff between sensitivity and bandwidth, with the transducer material impedance playing a key role. PZT (lead zirconate titanate) is a common material used in conventional ultrasound transducers. Although efficient in transduction of sound to electrical signal (and vice versa), PZT is a high density ceramic and has a characteristically high acoustic impedance compared to tissue. Acoustic energy tends to reflect off the tissue-PZT interface rather than be effectively coupled (transmitted or detected). Matching layers and backing material improve the coupling, at the expense of bandwidth and sensitivity. Modern materials (e.g., PMN, PZN single crystal and other materials) and processing techniques (such as composite materials) are improving the situation, but these coupling characteristics still present an issue for thermoacoustic imaging.

Although PZT, mechanically diced into individual elements, is a common material for constructing ultrasound transducers, other materials and structures are available.

PVDF (polymer vinylidine flouride) is a piezoelectric polymer that provides ultrasound transduction over a very wide range of frequencies, although with reduced transduction efficiency compared to piezoceramics. The material's acoustic impedance is lower compared to PZT, therefore providing a closer match to tissue and less loss entering the body. As a result, broad bandwidth is achievable without the need for complex, thin matching layers. PVDF is often used to construct ultrasound hydrophones, which, after calibration, can accurately measure acoustic pressures over a wide range of frequencies (e.g., for characterizing the output from ultrasound imaging arrays). A shortcoming of PVDF that prevents it from being more widely adopted as a transducer material is its somewhat weak performance as a electromechanical transmitter. For the receive-only transducer arrays for thermoacoustic imaging, however, PVDF may provide a good solution in that a dedicated transducer array primarily needs excellent receive efficiency and bandwidth. In addition to choice of substrate materials to construct the ultrasound transducer, coating materials and coating thicknesses may materially affect transducer performance, i.e., in thermoacoustic receive-only transducers Another characteristic in configuring ultrasound transducer arrays is geometry of transducer structures. Element geometry (dimensions of overall element and sub-dicing pattern); array geometry (number of elements, element pitch, kerf), and thickness all may have a material effect on performance of an ultrasound transmit-receive transducer and a thermoacoustic receive-only transducer. In one embodiment, individual array elements of the thermoacoustic receive-only array have larger overall element dimensions than typical in the art of thermoacoustic imaging.

In one embodiment the thermoacoustic transducer is configured to include a focusing element; alternatively the thermoacoustic transducer does not include a focusing element.

In one embodiment, the transmit-receive transducer array receives and detects echoes from an ultrasound beam delivered into the tissue by the transmit-receive transducer array, and converts the echoes to ultrasound output signals. The receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals. In this embodiment, the transmit-receive transducer array is not configured to detect thermoacoustically-generated acoustic signals in response to electromagnetic energy delivered into the tissue by a source of electromagnetic energy, and the receive-only transducer array is not configured to detect echoes from the ultrasound beam delivered into the tissue by the transmit-receive transducer array.

In another embodiment, the transmit-receive transducer array, the receive-only transducer array, or both of these arrays are configured to effect both modes of ultrasound detection: (a) receive and detect echoes from an ultrasound beam delivered into the tissue by the transmit-receive transducer array, and convert the echoes to ultrasound output signals; and (b) receive and detect thermoacoustically generated acoustic signals (ultrasound waves) in response to electromagnetic energy delivered into the tissue by a source of electromagnetic energy, and convert the thermoacoustically generated acoustic signals to thermoacoustic output signals. In an embodiment, the transmit-receive transducer array is multiplexed between a first mode of operation in which it delivers an ultrasound beam into the tissue, and converts echoes of the ultrasound beam to ultrasound output signals; and a second mode of operation in which it acts as a receive-only transducer. In the second mode of operation, the transmit-receive transducer array detects thermoacoustically generated acoustic signals in response to electromagnetic energy delivered into the tissue by a source of electromagnetic energy, and converts the thermoacoustically generated acoustic signals to thermoacoustic output signals. Dual mode operation of one or both of the transducer arrays may provide increased imaging efficiencies by extending the operational duty cycle of the dual mode array(s), while multiplexing avoids interference between the two modes of detection.

In one embodiment shown in FIG. 1, a composite ultrasound imaging system 102 for imaging a three dimensional volume of tissue includes a transmit-receive transducer array 106 and a receive-only transducer array 108. The transmit-receive array 106 may be contained within an ultrasound imaging probe 110 including an ultrasound housing 112, while the receive-only transducer array 108 may be contained within an thermoacoustic imaging probe 114 including a thermoacoustic housing 116. The transmit-receive array includes a plurality of transmit-receive array elements 106A, 106B, 106C, etc., wherein each transmit-receive array element is an individual physical region of a transmit-receive transducer that is capable of emitting an ultrasound beam into a three dimensional volume of tissue, and of receiving and detecting echoes from the ultrasound beam and converting the echoes to ultrasound output signals. Similarly, the receive-only transducer array 108 includes a plurality of receive-only elements 108A, 108B, 108C, etc., wherein each receive-only element is an individual physical region of a receive-only transducer that is capable of receiving and detecting thermoacoustically-generated acoustic signals in response to electromagnetic energy delivered into the tissue by a source of electromagnetic energy, and converting the thermoacoustically-generated acoustic signals to thermoacoustic output signals. In the composite ultrasound imaging system 102, the receive-only transducer array elements 108A, 108B, 108C are in registration with the transmit-receive array elements 106A, 106B, 106C.

FIG. 1 shows the transmit-receive transducer array 106 and a receive-only transducer array 108, without limiting the form of these arrays, array elements, and the form of ultrasound imaging probe 110 and thermoacoustic imaging probe 114, or the form of a unified ultrasound probe 104, containing these arrays. Transmit-receive transducer array 106 and a receive-only transducer array 108 can assume a wide variety of two dimensional (2d) array geometries as known in the art, for example including linear, curved linear, circular, square, and rectangular array geometries. Individual elements of the transmit-receive transducer array 106 and of the receive-only transducer array 108 can have various shapes, such as square, circular, elliptical, rectangular, and polygon. Transmit-receive ultrasound transducer arrays and receive-only transducer arrays can have a wide range of scales such as single elements, a few elements, dozens of elements, hundreds of elements or thousands of elements.

Although FIG. 1 illustrates three transmit-receive array elements 106A, 106B, 106C and three receive-only elements 108A, 108B, 108C, it is intended that any number of elements may be used in the transmit-receive array or the receive-only array. The embodiments disclosed herein are not intended to be limited to any particular number of transmit-receive array elements or receive-only elements or be limited to the number of transmit-receive array elements or receive-only elements shown in the figures.

In the composite ultrasound imaging system 102, each of the transmit-receive transducer array 106 and receive-only transducer array 108 may be formed across a flat surface, a convex surface, or a concave surface. Arrays formed on curved surfaces may be curved in one dimension, or curved in two dimensions. The transmit-receive array 106 and the receive-only array 108 each may comprise rigid or non-rigid structures. The composite ultrasound probe 104 may be mounted or disposed to a variety of mounting surfaces, e.g., curved, flat, or irregular mounting surfaces. In one embodiment, either or both the transmit-receive transducer array 106 and the receive-only transducer array 108 includes a conformal surface, which can conform to a tissue surface. The transmit-receive array 106 and the receive-only array 108 may be mounted to move together within an ultrasound probe or other housing; one of these arrays may be movable while the other array is stationary; or both arrays may be mounted in a stationary position. The imaging system may control motion of the transmit-receive array, the receive-only array, or both arrays, to scan the tissue in a desired imaging mode. For example, one or both transducer arrays may be scanned in a linear scan, a rectilinear scan pattern within a 2D plane, a rotational scan, and other scan patterns; and the transmit-receive array and receive-only array may be scanned in different scan patterns.

The components of an ultrasound probe, such as a unified ultrasound imaging probe 104, or separate ultrasound imaging probe 110 and thermoacoustic imaging probe 114, include a housing, a transducer array (or for unified probe 104, two transducer arrays) and internal wiring. The ultrasound probe may include other components such as a cable (e.g., to connect an ultrasound probe to an imaging assembly that receives output signals from the probe, or for charging a battery power source), signal processing circuitry, shielding, and battery power source. In an embodiment, unified ultrasound probe 104, or separate ultrasound imaging probe 110 and thermoacoustic imaging probe 114, may comprise a wireless ultrasound probe that omits the external cable.

In one embodiment of composite ultrasound imaging system 102, radiofrequency (RF) pulses are used as electromagnetic energy in thermoacoustic imaging, and the system shields the combined ultrasound transducer array from the radiofrequency (RF) pulses. RF pulses can interact with either a transmit-receive transducer or receive-only transducer in at least two ways. First, the electric field may produce a signal on the electrical leads connecting to the transducer element, either by direct electric field coupling to the leads, or by producing an electrical signal within the transducer material. This signal can be ignored by the data acquisition system, as it occurs prior to the acoustic signals being received from the tissue. In one embodiment, the system provides a period (typically microseconds) of ringdown time following excitation of the receive-only transducer, i.e., to allow vibration of the transducer to decrease to a negligible level. Second, where using radiofrequency (RF) pulses as excitation source, the transducer may produce an acoustic pulse in response to the impressed electric field. This acoustic pulse propagates into the body under examination and some acoustic energy is scattered and returned to the receiving transducer, appearing as a spurious signal.

In an embodiment, in order to reduce or minimize these effects of RF energy penetrating the composite transducer housing, the composite transducer and its signal cable should be shielded against the specific RF energy to minimize the RF pickup. This shielding can take the form of an electrically conductive and continuous layer covering the entire transducer and cable to the point of signal detection (typically the data acquisition system). In the cable, this can be provided by shielding technologies such as a combination of one or more braided conductive wire sheath(s), aluminized Mylar foil wrap, and coaxial cable. The shielding around the transducer itself may be acoustically transparent, and may form one common terminal of the transducer element(s). Advantageously, the shielding layer thickness has a sufficient number of skin depths at the RF frequency to provide adequate attenuation.

In an embodiment, the ultrasound imaging probe 110 and thermoacoustic imaging probe 114 are combined in a single ultrasound probe 104; in this embodiment arrow "A" and reference numeral 104 indicate the combination of the upper and lower structures in a unified probe. The components of unified ultrasound probe 104 may include all components of the assemblies shown at 110 and 114 in FIG. 1. The ultrasound probe 104 may include a single housing for all transducer structures, or may include an ultrasound housing 112 that houses the transmit-receive transducer array 106, and an thermoacoustic housing 116 that houses the receive-only transducer array 108. The transmit-receive transducer array 106 is in registration with the receive-only transducer array 108 within the ultrasound probe 104. In one embodiment, the receive-only transducer array 108 comprises an inner structure of the ultrasound probe 104, and the receive only transducer array comprises an outer structure of the ultrasound probe 104, surrounding the transmit-receive transducer array 106. In this configuration, the receive-only transducer array 108 may be disposed at the surface of the ultrasound probe 104, closest to tissue to be imaged, a physical arrangement that can improve the sensitivity of the receive-only transducer array 108 in thermoacoustic imaging.

In addition to the components of a unified ultrasound probe 104, the combined imaging system 102 includes additional components shown collectively at 122. The additional components 122 can include for example an imaging assembly for processing thermoacoustic output signals from the receive-only transducer array 108 and ultrasound output signals from transmit-receive transducer array 106, to generate images of structures of tissue; a source of electromagnetic energy to be delivered into the tissue to thermoacoustically generate acoustic signals at excitation sites within the tissue; and other mechanical and electrical components of a combined ultrasound and thermoacoustic imaging system.

In one embodiment, the thermoacoustic imaging probe 114 is provided as part of an thermoacoustic imaging system that is designed to be added to an existing ultrasound imaging system including the ultrasound imaging probe 110 with transmit-receive array 106. In this embodiment, arrow "A" and reference numeral 104 indicate mechanically joining thermoacoustic probe 114 to ultrasound probe 110 to form a combined probe assembly 104. The receive-only transducer array 108 of the sleeve is registered with the transmit-receive transducer array 106 within the combined probe assembly 104. In an embodiment, thermoacoustic probe 114 and ultrasound probe 110 each may have separate housings, internal wiring, external cabling, and optionally other structures such as internal electronics and shielding. In one embodiment, connection of thermoacoustic probe 114 to ultrasound probe 110 involves both mechanically joining but not electrically interconnecting these probes. In another embodiment, connection of thermoacoustic probe 114 to ultrasound probe 110 involves both mechanically joining and electrically interconnecting these probes. In an embodiment, thermoacoustic probe housing 116 takes the form of a sleeve that is mechanically joined around the ultrasound probe housing 112 of the existing ultrasound imaging system.

In addition to the components of thermoacoustic probe 114, the thermoacoustic imaging system includes additional components shown collectively at 122, designed to be added to an existing ultrasound imaging system to provide a combined imaging system 102. The additional components 122 of the thermoacoustic imaging system can include for example an imaging assembly for processing thermoacoustic output signals from the receive-only transducer array 108 of the thermoacoustic probe 114, and ultrasound output signals from transmit-receive transducer array 106 of the existing ultrasound probe 110, to generate composite images of structures of tissue. As another example, the thermoacoustic imaging system can include a source of electromagnetic energy to be delivered into the tissue to thermoacoustically generate acoustic signals at excitation sites within the tissue.

The imaging assembly receives ultrasound output signals from the ultrasound imaging probe 110 (or unified probe 104), receives thermoacoustic output signals from the thermoacoustic imaging probe 114 (or unified probe 104), and analyzes these signals through signal processing in order to provide information on the features of tissue. In an embodiment, the imaging assembly digitizes the ultrasound output signals and the thermoacoustic output signals and processes the digitized signals to provide imaging information representative of the ultrasound output signals and the thermoacoustic output signals. In an embodiment, the imaging assembly uses data representative of known geometry and positions of elements of the transmit-receive transducer array and the receive-only transducer array in reconstructing respective images (ultrasound and thermoacoustic) from the thermoacoustic output signals and the ultrasound output signals. The results can be displayed to the user as depth profile plots, or as 2-, 3-, or 4-dimensional images, among other image formats. In an embodiment, the imaging assembly provides composite images representative of the ultrasound output signals and the thermoacoustic output signals. In an embodiment, imaging assembly 122 includes a housing separate from the housings of the ultrasound imaging probe 110 and the thermoacoustic imaging probe 114 (or single housing of unified probe 104), and the imaging probe housing(s) may be tethered to the housing of imaging assembly 122.

In an embodiment, the registration of the receive-only transducer array 106 with the transmit-receive transducer array 108 in the composite ultrasound imaging system 102 uses data representative of known geometry and positions of elements of the two arrays in reconstructing respective images (ultrasound and thermoacoustic) from the thermoacoustic output signals and the ultrasound output signals. Another aspect of the registration of the receive-only transducer array 106 with the transmit-receive transducer array 108 is physical alignment or proximity of the elements of these two arrays, which proximity creates a tendency of the two arrays to image the same regions or structures of tissue for purposes of composite imaging of these regions or structures.

Figure 2:
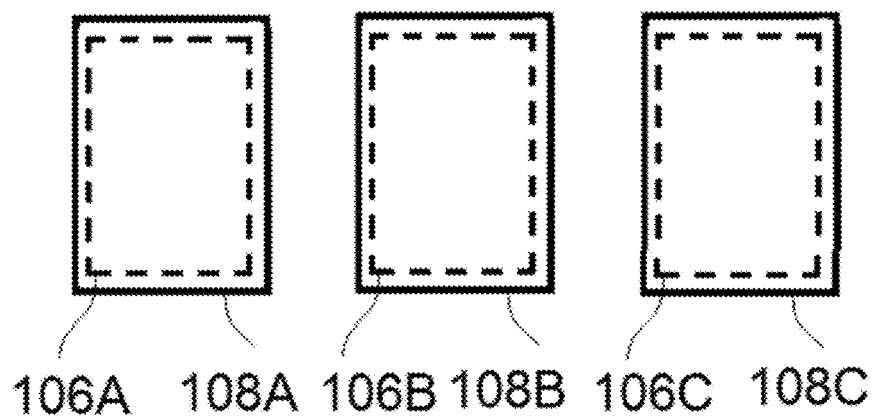
FIG. 2 illustrates a combination transducer array, according to an exemplary embodiment.
Figure 3:
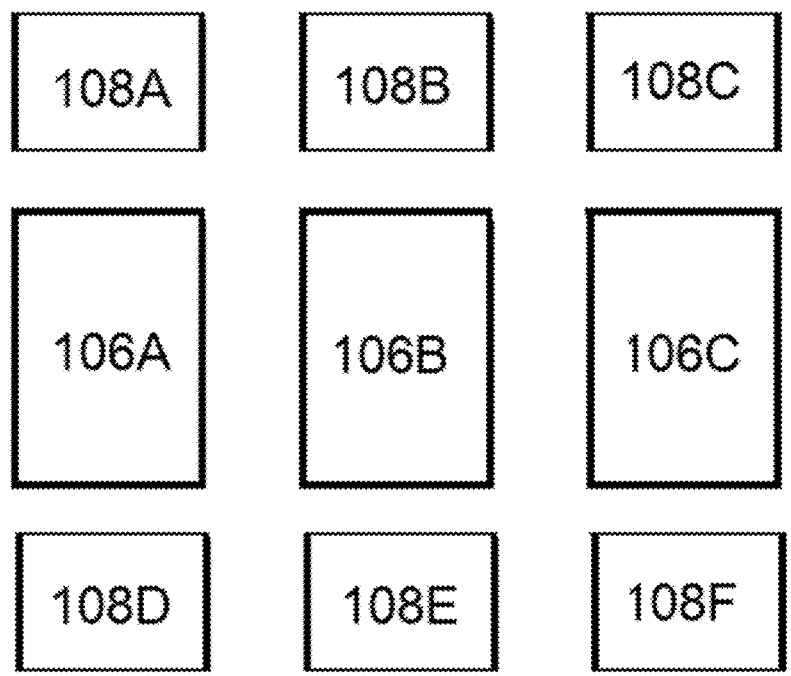
FIG. 3 illustrates a combination transducer array, according to an exemplary embodiment.

FIGS. 2 and 3 schematically illustrate approaches for physical alignment or proximity of elements of the transmit-receive transducer array 106 and elements of the receive-only transducer array 108. In FIG. 2, transducer arrays 106, 108 form two layers of array elements, with the receive-only array elements 108A, 108B, 108C covering and generally aligned with the transmit-receive array elements 106A, 106B, 106C. The physical alignment of individual array elements of array 106 with individual elements of array 108 may involve substantially complete overlap of the respective elements, or less than complete overlap of the array elements. In this arrangement, the ultrasound waves transmitted by transmit-receive array elements 106A, 106B, 106C may "shoot through" the receive-only transducer array elements 108A, 108B, 108C. In one embodiment, the receive-only transducer array elements 108A, 108B, 108C are tuned to be insensitive to the ultrasound energy transmitted through this transducer array.

Another approach for physical alignment or proximity of elements of the receive-only transducer array 108 with elements of the transmit-receive transducer array 106 is in providing a two dimensional (2d) or planar pattern of these arrays. In the composite ultrasound imaging system 102, the receive-only transducer array may form a 2d pattern that surrounds the transmit-receive transducer array 106 on one or more sides. For example as seen in FIG. 3, two linear arrays 108A-108C and 108D-108F of receive-only array elements are disposed at opposite sides of a linear array of transmit-receive array elements 106A-106C. Other two dimensional (2d) patterns of transmit-receive array and receive-only array are possible in providing composite imaging. For example, in an inversion of the pattern described above, the transmit-receive transducer array may form a 2d pattern that surrounds the receive-only transducer array 106. In other types of 2d pattern of array elements, elements of the receive-only transducer array may be interspersed with or interleaved with elements of the transmit-receive transducer array.

In addition to physically registering elements of the receive-only transducer array 108 with elements of the transmit-receive transducer array 106, the composite ultrasound imaging system may use data representative of known geometry and positions of elements of the two arrays in algorithms for reconstructing respective images (ultrasound and thermoacoustic). In one embodiment, an algorithm of an algorithm for reconstructing the respective images uses the same image coordinate system in data representing the respective images, and thermoacoustic imaging data and ultrasound imaging data are reconstructed in that same image coordinate system. In another embodiment, an algorithm for reconstructing the respective images uses first and second image coordinate systems in data representing the respective images. For example, thermoacoustic imaging data may be reconstructed into the first image coordinate system, and ultrasound imaging data may be reconstructed into the second image coordinate system. In forming composite images, data in the first image coordinate system may be transformed into data in the second image coordinate system, and vice versa.

The composite ultrasound imaging system may generate composite images that combine ultrasound images associated with given echo locations within the tissue, with thermoacoustic images associated with thermoacoustic excitation sites located at or near the echo location. In a composite ultrasound imaging example, composite images include first image components representing locations of features of tissue generated from the ultrasound output signals, and second image components representing functional characteristics of the features of tissue generated from the thermoacoustic output signals.

One way in which the physical registration of the transmit-receive transducer array and the receive-only transducer array may be related to registration of imaging data generated by these arrays is in association of array elements with channels (electronic data channels) in the composite imaging system electronics. In one embodiment, each element of the transmit-receive transducer array is associated with a single channel of the imaging system, and each element of the receive-only transducer array is associated with a single channel of the imaging system. In another embodiment, multiple elements of the transmit-receive transducer array are associated with a single channel of the imaging system. In another embodiment, multiple elements of the receive-only transducer array are associated with a single channel of the imaging system. In an embodiment of the ultrasound imaging system with unified ultrasound probe, one or more elements of the transmit-receive transducer array, in combination with one or more elements of the receive-only transducer array, are associated with a single shared channel of the ultrasound imaging system.

FIG. 17 shows a method for operating an ultrasound imaging system to image features of tissue. At 1702, the method provides a combination transducer array with transmit-receive array elements and with receive-only array elements. The combination transducer array may be provided as part an integral ultrasound imaging system or may be provided by adding an thermoacoustic imaging probe and other components of an thermoacoustic imaging system to a preexisting ultrasound imaging system. In one embodiment, at 1702, the combined arrays are housed within a single ultrasound imaging probe. In another embodiment, the transducer array with transmit-receive array elements is housed within an ultrasound imaging probe, and the transducer array with receive-only array elements is housed within a thermoacoustic imaging probe.

Step 1704 registers the receive-only array elements with the transmit-receive array elements. This step may employ a variety of approaches for registering receive-only array elements with transmit-receive array elements, as described in the present disclosure. In an embodiment, registering the receive-only array elements with the transmit-receive array elements involves physical alignment and proximity of given receive-only array elements with given transmit-receive array elements. In another embodiment of registering the receive-only array elements with the transmit-receive array elements, the composite ultrasound imaging system stores data representative of known geometry and positions of elements of the two arrays, and uses this data in reconstructing respective images (ultrasound and thermoacoustic). In an embodiment of step 1704, these approaches to registering the receive-only array elements with the transmit-receive array elements are combined. The receive-only array elements may be registered with the transmit-receive array elements in an ultrasound imaging system with a unified ultrasound probe, or the receive-only array elements may be registered with the transmit-receive array elements in adding a thermoacoustic imaging system to a preexisting ultrasound imaging system. In a further embodiment, the receive-only array elements may be registered with the transmit-receive array elements during calibration of a combined ultrasound imaging system.

At 1706, the receive-only transducer array detects acoustic signals thermoacoustically-generated in response to electromagnetic energy delivered into the tissue by a source of electromagnetic energy, and converts the detected thermoacoustically-generated acoustic signals to thermoacoustic output signals. At 1708, the transmit-receive transducer array delivers an ultrasound beam to the tissue, detects echoes of the ultrasound beam from the tissue, and converts the detected echoes to ultrasound output signals.

At 1710, the ultrasound imaging system including the combination transducer array generates a composite image of the tissue from the thermoacoustic output signals and the ultrasound output signals. The ultrasound imaging system may use data representative of known geometry and positions of elements of the transmit-receive transducer array and the receive-only transducer array in algorithms for reconstructing respective images (ultrasound and thermoacoustic). Other imaging techniques may be employed, such as scanning one or both transducer arrays, e.g., in 2D or 3D imaging; dynamic imaging based upon a series of images received over time; composite imaging that combines structural and functional imaging; etc.

As described below, a combined ultrasound imaging system may incorporate various geometries of the transmit-receive array, and various geometries of the receive-only array. The geometry of the transmit-receive array may be selected to provide a desired mode of ultrasound imaging, and the geometry of the transmit-receive array may be selected to provide a desired mode of thermoacoustic imaging. Furthermore, the combination of array geometries may be selected to provide desired composite imaging modes. Additionally, the transmit-receive array and the receive-only array may be mounted within an imaging probe or other housing to permit motion of either of these arrays, and either or both arrays may be scanned during imaging.

The geometry, and optionally the scanning, of the transmit-receive transducer array may be chosen to provide various modes of ultrasound imaging. A-mode (amplitude mode) ultrasound employs a single transducer to scan a line through the tissue with the echoes plotted as a function of depth. B-mode (brightness mode) ultrasound, also called 2D mode, employs a linear array of transducers to simultaneously scan a plane through the tissue that can be viewed as a two-dimensional image. C-mode ultrasound forms images in a plane normal to an A-mode line. The imaging system selects data from a specific depth of the A-mode scan, then the ultrasound transducer is moved in the 2D plane at this fixed depth to sample the entire area. In M-mode (motion mode) ultrasound, pulses are emitted in quick succession—each time, either an A-mode or B-mode image is taken. Over time, M-mode ultrasound is analogous to recording a video in ultrasound.

Similarly the geometry, and optionally the scanning, of the transmit-receive transducer array may be chosen to provide various modes of thermoacoustic imaging. In thermoacoustic imaging, for any given time-of-flight, a given transducer will receive the sum of the thermoacoustic waves originating at excitation sites at the same distance from the transducer considered as a point. The receive-only array geometry, and any scanning of the transducer array, may be chosen to resolve ambiguity that can arises when attempting to localize an excitation site with a point transducer. For example, linear transducer receive-only arrays, both curved and straight, may be employed in 2D thermoacoustic imaging of tissue. Thermoacoustic signals within an imaging plane can be localized by calculating the times-of-flight from each position within the plane to each element of the linear receive-only array. A 2D array of receive-only elements may be employed to image a tissue volume in three dimensions (3D). Analogously to M-mode ultrasound, in thermoacoustic imaging electromagnetic energy may be transmitted to the tissue to provide a series of excitations over time, wherein each time resultant acoustic pulses are captured by the receive-only transducer array and used to generate dynamic thermoacoustic images.

Figure 4:
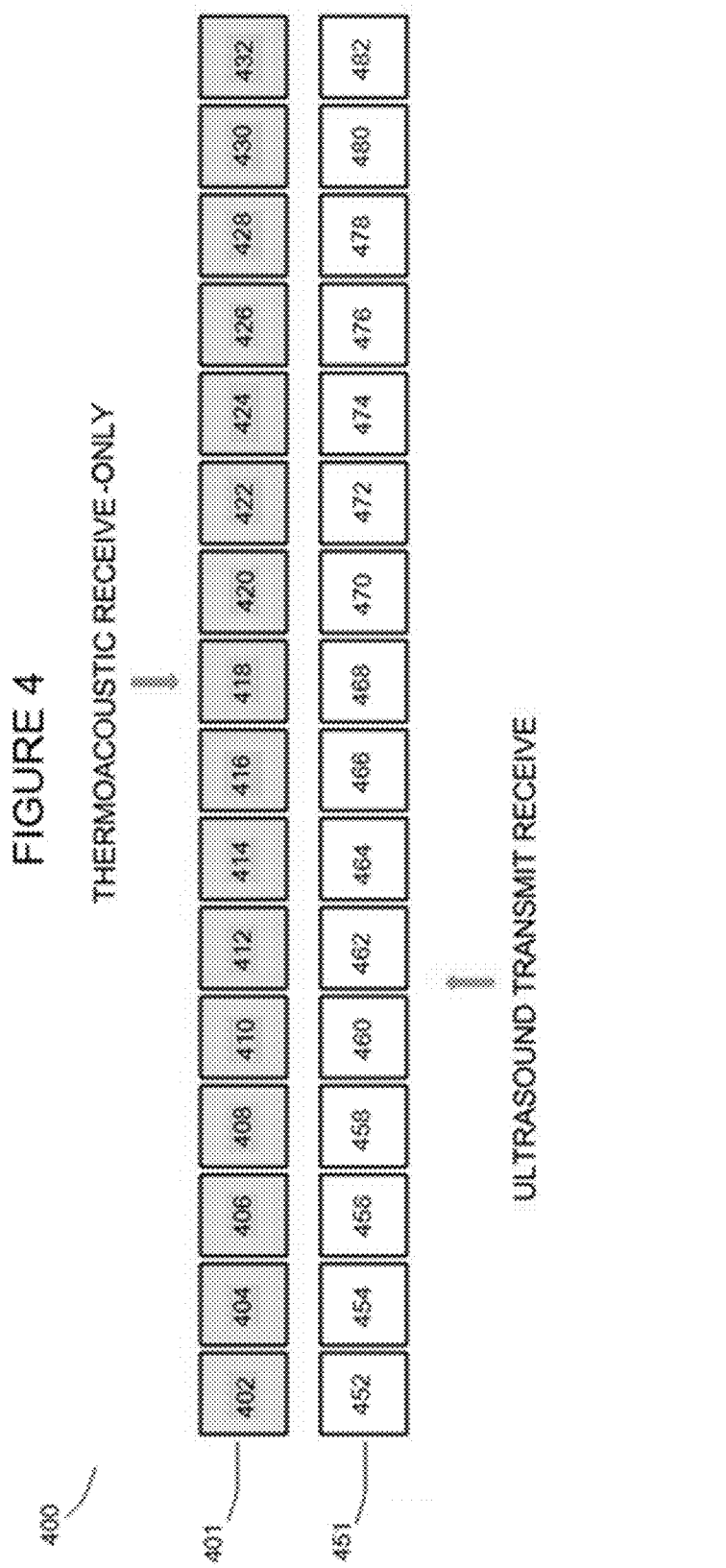
FIG. 4 illustrates a combination transducer array, according to an exemplary embodiment.
Figure 5:
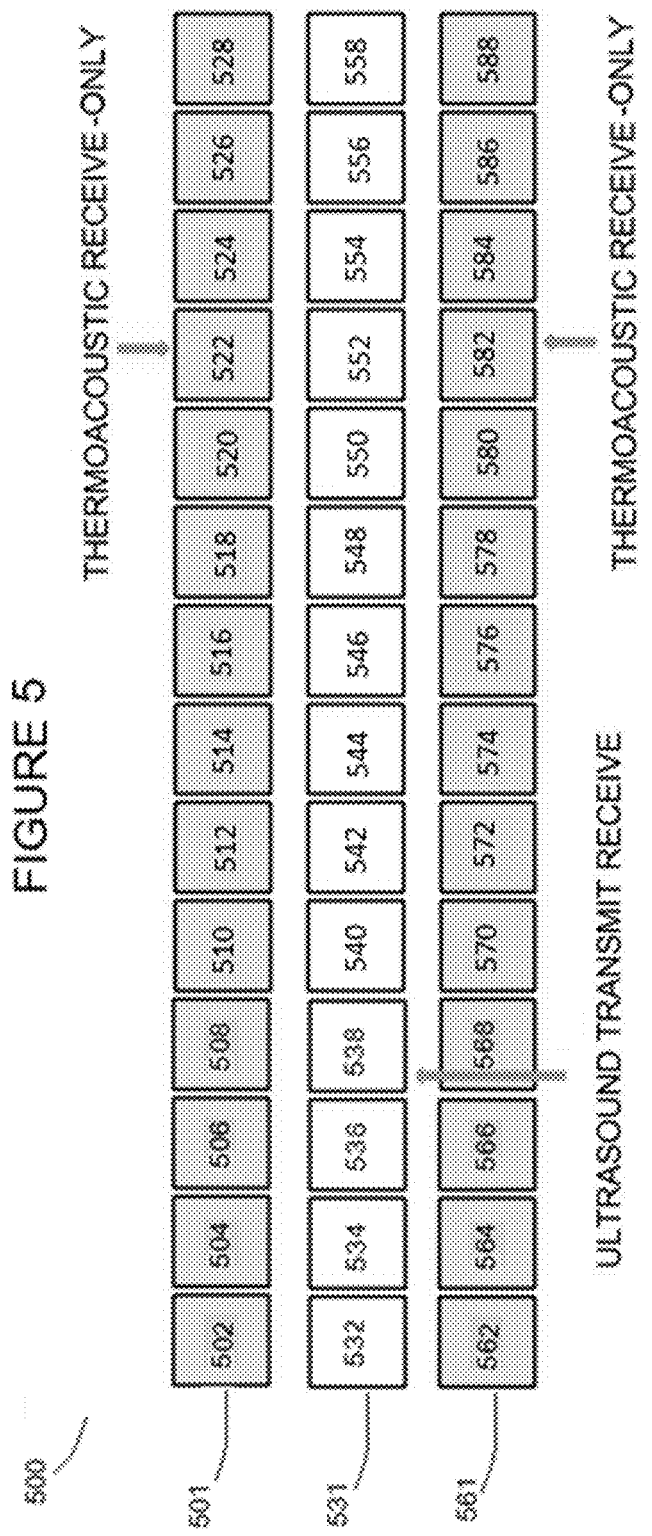
FIG. 5 illustrates a combination transducer array, according to an exemplary embodiment.
Figure 6:
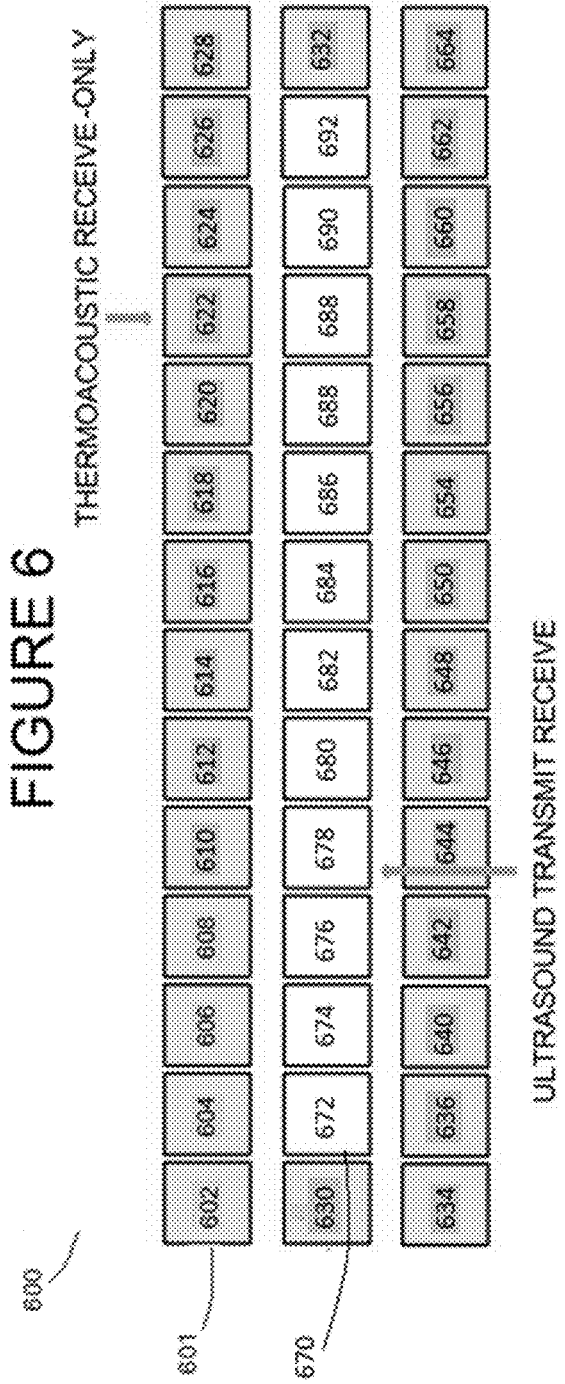
FIG. 6 illustrates a combination transducer array, according to an exemplary embodiment.

FIGS. 4-6 show various embodiments of combination transducer array including an ultrasound transmit-receive array in the form of a linear array, with various forms of a thermoacoustic receive-only array surrounding the ultrasound transmit-receive array. The combination transducer array 400 of FIG. 4 includes a linear transmit-receive array 451 with individual array elements 452, 454, 456, etc. A linear receive-only transducer array 401 with individual array elements 402, 404, 406, etc. surrounds the transmit-receive array 451 on one side. The combination transducer array 500 of FIG. 5 includes a linear transmit-receive array 531 with individual array elements 532, 534, 536, etc. Two linear receive-only transducer arrays surround the transmit-receive array 531 on opposite sides, including a first linear receive-only array 501 with individual array elements 502, 504, 506, etc., and a second linear receive-only array 501 with individual array elements 502, 504, 506, etc. The combination transducer array 600 of FIG. 6 includes a linear transmit-receive array 670 with individual array elements 672, 674, 676, etc. A rectangular loop array of receive-only transducer array elements 601 including individual array elements 602, 604, 606, etc. surrounds the linear transmit-receive array on all four sides.

Figure 7:
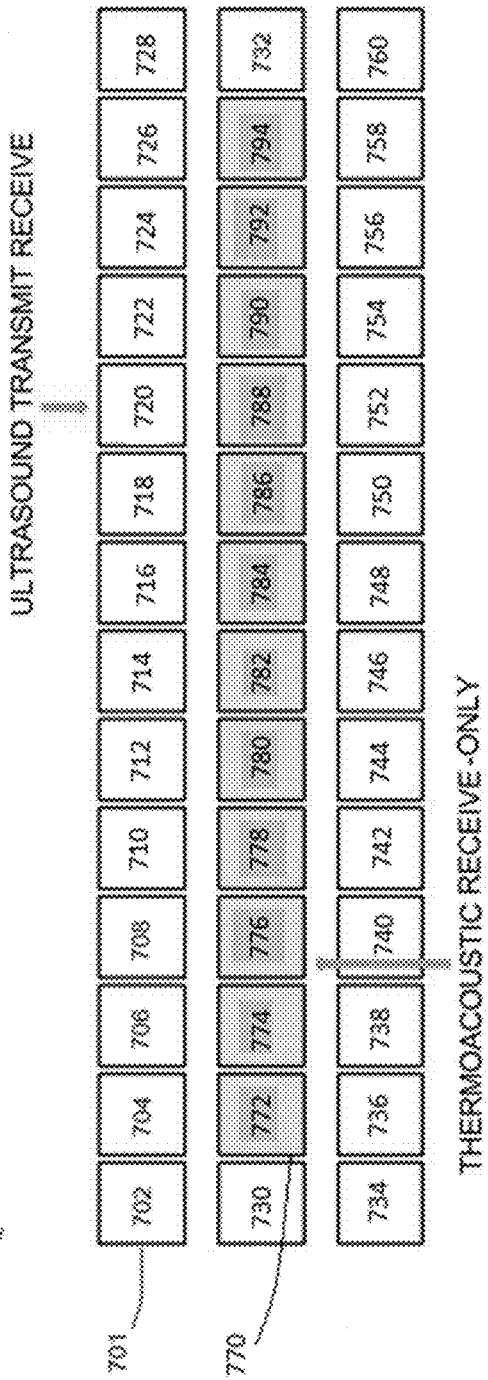
FIG. 7 illustrates a combination transducer array, according to an exemplary embodiment.

The combination transducer array 700 of FIG. 7 is similar to the array 600 of FIG. 6, but inverts the geometric relationship of the receive-only transducer array and the transmit-receive transducer array. Combination transducer array 700 includes a linear receive-only array 770 with individual array elements 772, 774, 776, etc. A rectangular loop array of transmit-receive transducer array elements 701 including individual array elements 702, 704, 706, etc. surrounds the linear transmit-receive array on all four sides.

In the embodiments shown in FIG. 4-6, the transmit-receive transducer has a two dimensional (2d) configuration as a linear array. Exemplary 2d configurations of the receive-only array in conjunction with a linear transmit-receive array include for example: (a) single linear array, adjacent one side of the linear transmit-receive array; (b) dual linear arrays, adjacent two sides of the linear transmit-receive array; (c) rectangular loop array, surrounding the linear transmit-receive array; and (d) rectangular dense array surrounding the linear transmit-receive array.

FIGS. 8, 9, 13 and 14 illustrate alternative embodiments for registering an transmit-receive transducer arrays with receive-only transducer arrays through the patterning of these arrays in two dimensions. In this variation, the transmit-receive array elements are interspersed or interleaved with the receive-only array elements. The transmit-receive array elements may be interspersed or interleaved with the receive-only array elements in a regular pattern, or irregular pattern. The regular or irregular pattern may include single array elements, or patches or series of array elements. For example, interleaved or interspersed patterns of array elements may include alternating rows of transmit-receive and receive-only array elements; alternating rectangular patches of transmit-receive and receive-only array elements; alternating individual array elements; and a sparse array of one type of array element interspersed with a dense array of the other type of array element.

Figure 8:
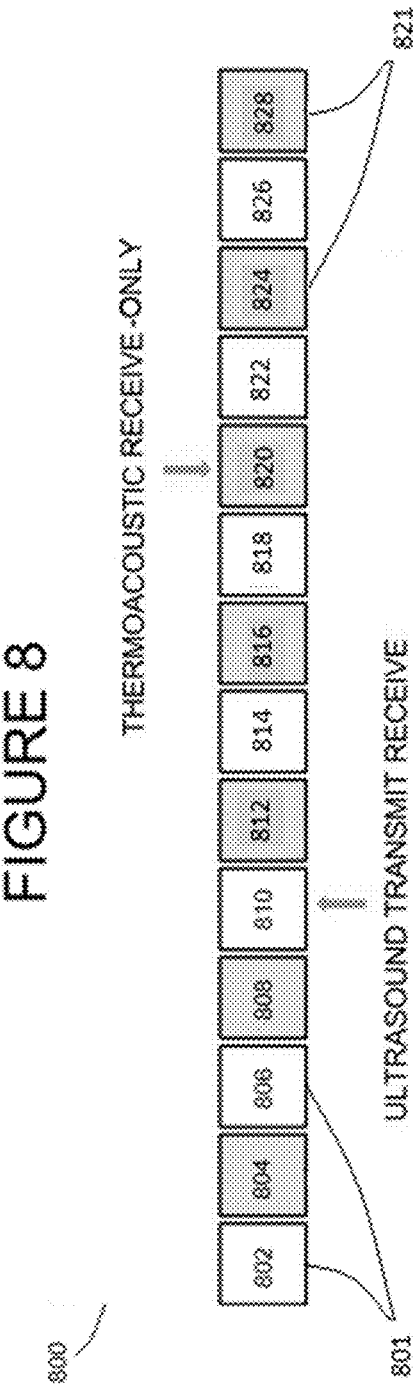
FIG. 8 illustrates a combination transducer array, according to an exemplary embodiment.

In the linear combination transducer array 800 of FIG. 8, an array 801 of transmit-receive array elements is interleaved in one dimension with an array 821 of receive-only array elements. In this interleaved pattern, individual array elements 802, 806, 810, etc. of transmit-receive array 801 alternate with individual array elements 804, 808, 812, etc. of receive-only array 821. The linear combination transducer array 900 of FIG. 9 represents another pattern in which elements of an array 901 of transmit-receive array elements are interleaved in one dimension with elements of an array 921 of receive-only array elements. In the interleaved pattern of transducer array 900, a series of array elements 902, 904, 906, 908. of transmit-receive array 901 is followed by series of array elements 922-936. of transmit-receive array 921. The series of array elements 922-936 of transmit-receive array 921 is followed by another series of array elements 910, 912, 914, 916 of transmit-receive array 901.

Figure 13:
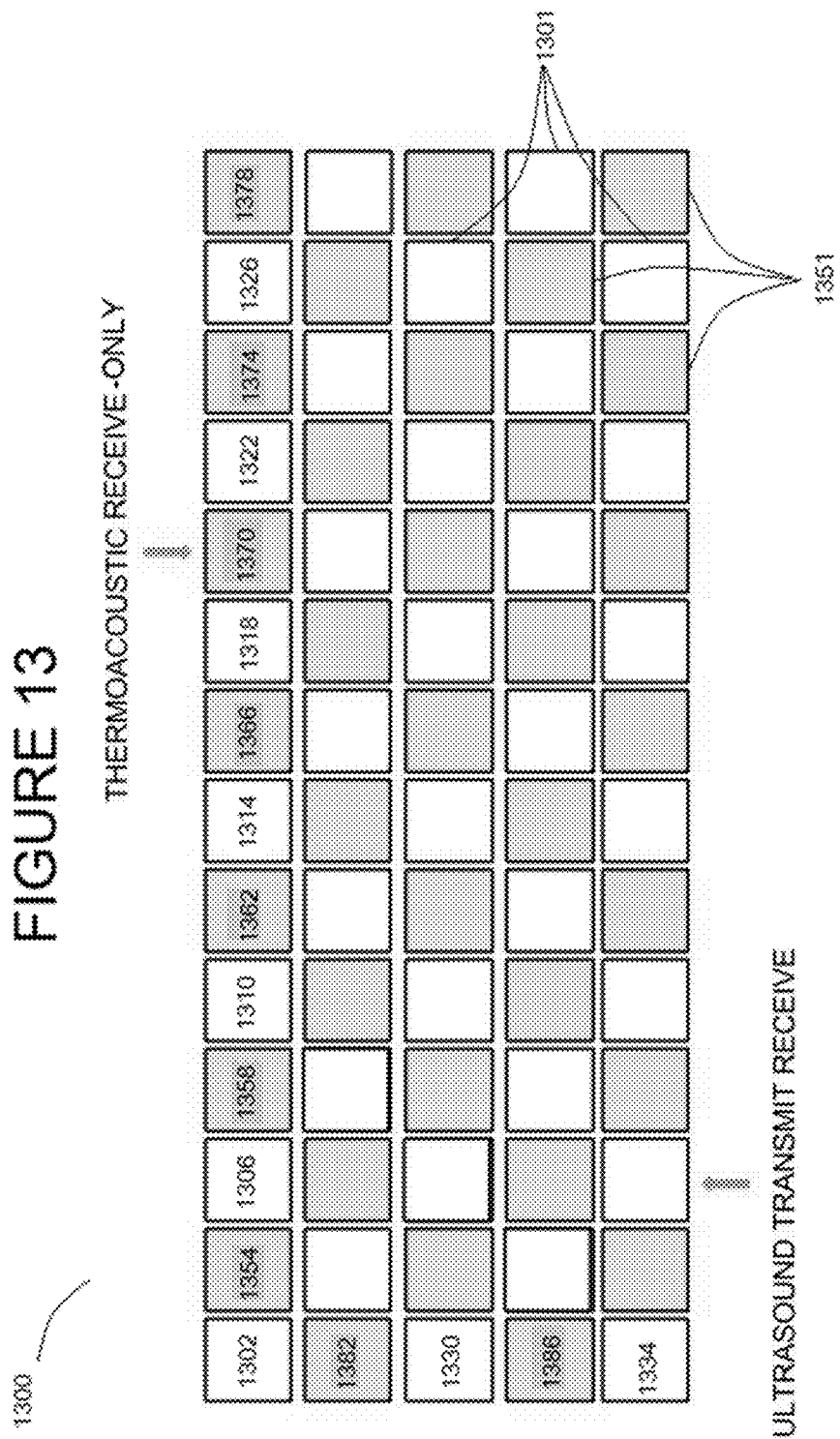
FIG. 13 illustrates a combination transducer array, according to an exemplary embodiment.
Figure 14:
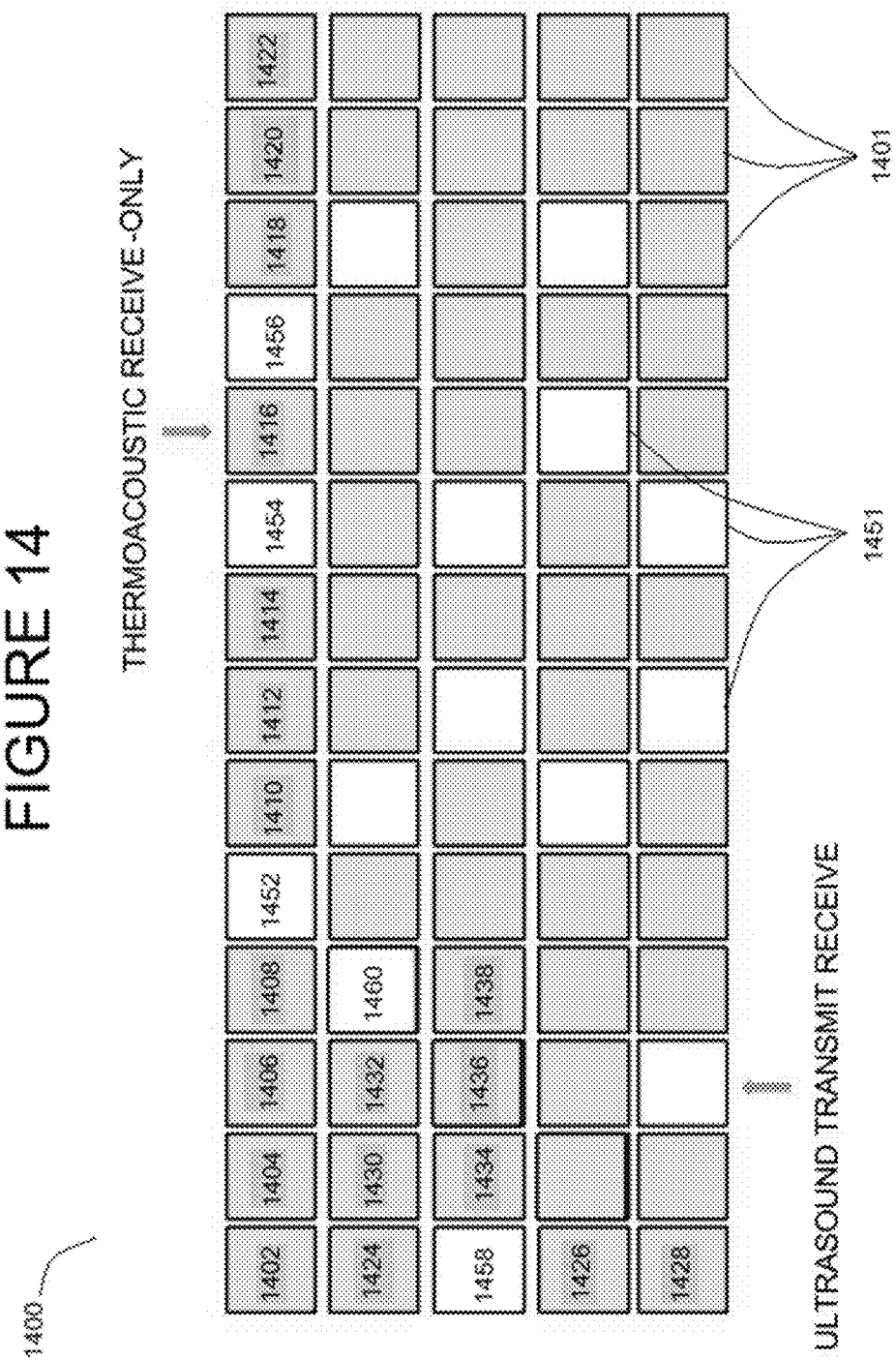
FIG. 14 illustrates a combination transducer array, according to an exemplary embodiment.

In the rectangular array 1300 of FIG. 13, an array 1301 of transmit-receive array elements is interleaved in two dimensions with an array 1351 of receive-only array elements. In this interleaved pattern, individual array elements 1302, 1306, 1310, etc. of the transmit-receive array 1301 alternate within individual array elements 1354, 1358, 1362, etc. of the receive-only transducer array 1351, in a checkered pattern with elements alternating both horizontally and vertically. Like the one dimensional interleaved pattern of combination transducer 800 of FIG. 8, the 2d pattern of combination transducer 1300 of FIG. 13 is a regular interleaved or interspersed pattern of array elements. FIG. 14 provides an example of an irregular pattern of rectangular transducer array 1400, in which transmit-receive array elements are interspersed within an array of receive-only elements. The array 1401 of receive-only array elements is a relatively dense array (greater than 50% of total array elements), while the array 1451 of transmit-receive array elements is a relatively sparse array (less than 50% of total array elements) of elements irregularly interspersed within the dense array.

In certain embodiments, the transmit-receive array has a two-dimensional configuration as a rectangular array. The transmit-receive array may be configured as a square array, or as a rectangular array with unequal sides. Exemplary 2d configurations of the receive-only array in combination with a rectangular transmit-receive array include: (a) one sided linear array, adjacent the rectangular transmit-receive array; (b) two sided linear array, adjacent three sides of the rectangular transmit-receive array; (c) rectangular loop array, surrounding the rectangular transmit-receive array; and (d) rectangular dense array, with two or more rows surrounding the rectangular transmit-receive array.

Figure 12:
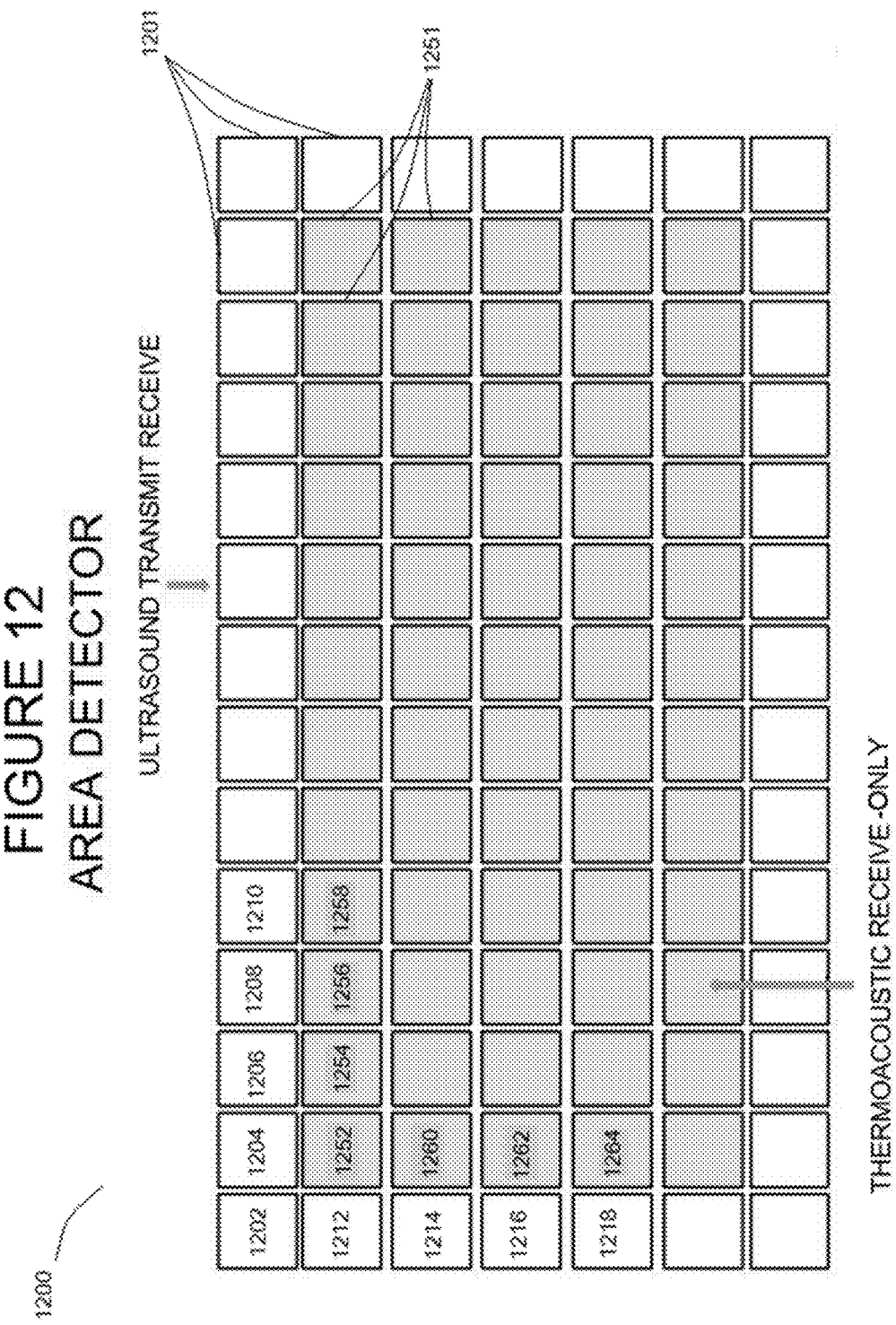
FIG. 12 illustrates a combination transducer array, according to an exemplary embodiment.

One application of rectangular ultrasound arrays is sometimes called area detectors, arrays adapted to sensing features (such as locations, functional characteristics, and dynamic properties) within areas of objects such as three dimensional volumes of tissue. FIG. 12 shows an example of an combination area detector 1200 including a rectangular dense array 1251 of thermoacoustic receive-only array elements 1252, 1254, 1256, etc. Thermoacoustic receive-only array 1251 is surrounded by a rectangular loop array 1201 of ultrasound transmit-receive array elements, including array elements 1202, 1204, 1206, etc. In forming a composite image using the combination area detector 1200, individual elements or patches of elements within the rectangular dense thermoacoustic array 1251 may be registered with individual elements or patches of elements within the rectangular loop ultrasound array 1201.

FIG. 10 and FIGS. 11A-B illustrate circular arrays of transmit-receive transducer elements and receive-only array elements, wherein circular arrays are another commonly known form of ultrasound array. In the combination transducer array 1000 of FIG. 10, the transmit-receive array 1005 comprises an array or concentric rings 1004, 1006, sometimes referred to as an annular array. The receive-only array 1001 comprises concentric rings 1002, 1006 and circular element 1010 interleaved with the transmit-receive array elements. In the combination transducer array 1100 of FIG. 11A, ultrasound transmit-receive array 1101 and thermoacoustic receive-only array 1131 are annular arrays, in which transmit-receive array 1101 is an outer array of multiple rings, and receive-only array 1131 is an inner array of multiple rings (annular array). FIG. 11B shows transmit-receive transducer array 1101 (with array elements 1102, 1104, etc.) and receive-only transducer array 1131 (with array elements 1132, 1134, etc.) in a side view. In further embodiments of circular combination transducer arrays, a thermoacoustic array of receive-only array elements may include single or multiple rings (each composed of multiple elements) surrounding a circular array of transmit-receive elements.

FIG. 15A shows in a side schematic view, and FIG. 15B shows a plan view, wherein a ultrasound imaging system 1500 includes an ultrasound probe 1510 housing an array 1520 of transmit elements (array elements configured for ultrasound transmit-receive properties) and an array 1530 of receive-only elements. In imaging system 1500, the transmit array is configured only to transmit ultrasound energy (transmit-only operation), while the receive-only array 1530 is configured to operate as a receiver in both ultrasound and thermoacoustic imaging modes. Receive-only array 1530 may constitute a hybrid array of "receive" elements including a mixture of elements configured for ultrasound imaging, and elements configured for thermoacoustic imaging. Advantageously, the receive-only array elements 1530 configured for ultrasound imaging may have a narrow bandwidth, while the receive-only array elements 1530 configured for thermoacoustic imaging may have a broad bandwidth.

The ultrasound probe 1510 is disposed in proximity to tissue 1540. The array 1520 of transmit elements and array 1530 of receive elements form two layers wherein the receive-only array elements are located at the probe surface (closest to tissue 1540), and the transmit array elements are located behind the receive elements. (In FIGS. 15A and 15B the light shading of the receive array and dark shading of the transmit array is in reverse to the shading of transmit-receive arrays and receive-only arrays in other drawings). The surface location of receive-only array 1530 can improve the sensitivity of the receive-only transducer array elements operating for thermoacoustic imaging. As seen in FIG. 15B, individual receive array elements substantially overlap individual transmit elements. The ultrasound waves transmitted by transmit array 1520 "shoot through" the receive-only transducer array 1530.

Figure 16A:
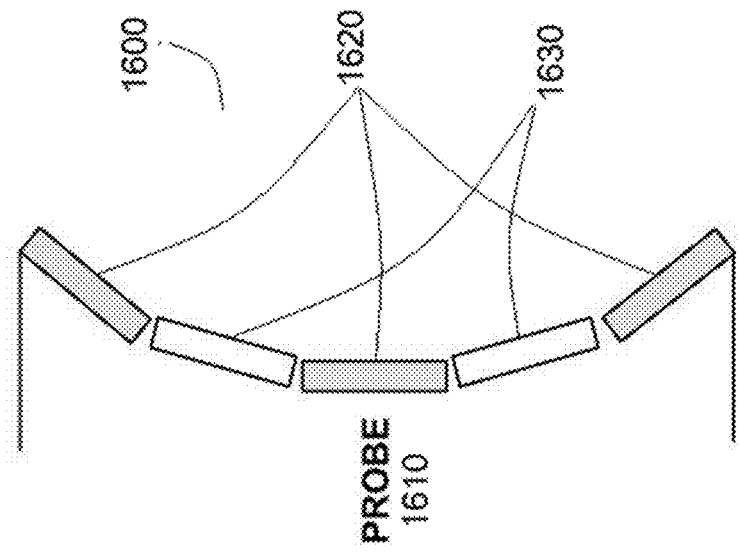
FIG. 16A is a perspective view of a combination transducer array, according to an exemplary embodiment.
Figure 16B:
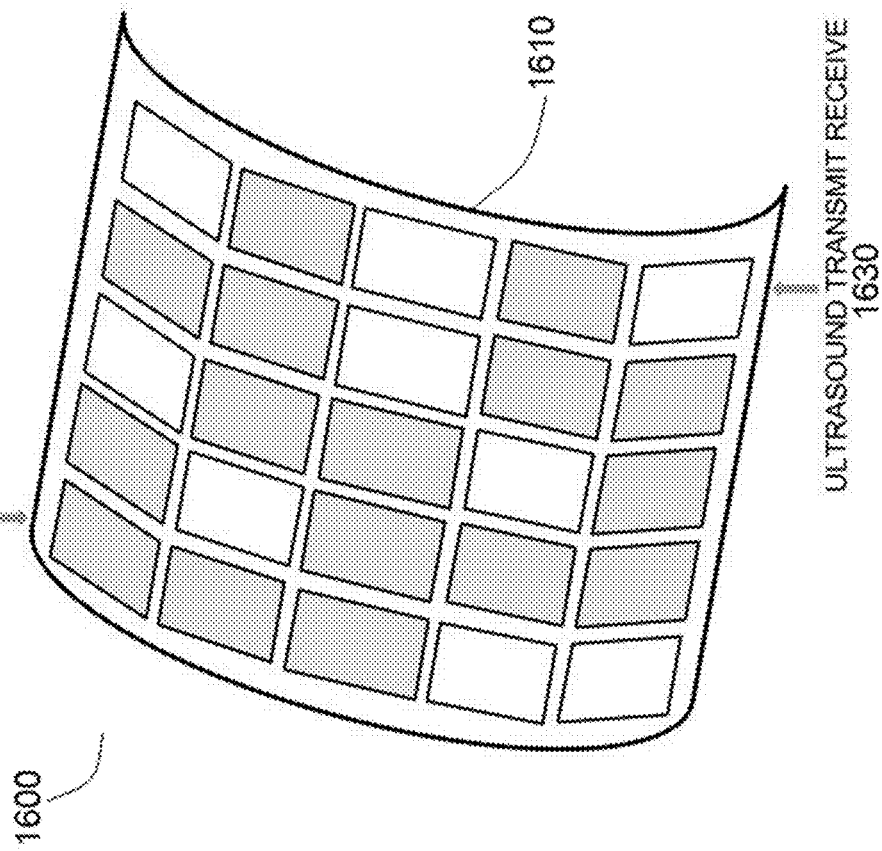
FIG. 16B is a side view of the combination transducer array of FIG. 16A.

FIGS. 16A and 16B show an embodiment of combination transducer 1600 including an ultrasound probe 1600 that is formed with a curved surface (curved in one direction). Probe 1600 houses a rectangular array of receive-only array elements 1620 and transmit-receive array elements 1630. These array elements are interspersed in an irregular array, in which the receive-only array elements form a relatively dense array and the transmit-receive array elements 1630 form a relatively sparse array.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A thermoacoustic imaging system for use in combination with an existing ultrasound imaging system for imaging features of tissue, the existing ultrasound imaging system including a transmit-receive transducer array comprising a plurality of transmit-receive array elements housed within a first ultrasound probe, wherein the transmit-receive transducer array receives and detects echoes from an ultrasound beam delivered into the tissue by the transmit-receive transducer array, and converts the echoes to ultrasound output signals, the thermoacoustic imaging system comprising:
   a source of electromagnetic energy;
   a receive-only transducer array comprising a plurality of receive-only array elements housed within a second ultrasound probe, wherein the second ultrasound probe, in a form of a sleeve, surrounds and is joined mechanically to the first ultrasound probe such that the plurality of receive-only array elements are configured to surround and are in physical alignment and in proximity to the plurality of transmit-receive array elements,
      wherein the plurality of receive-only array elements are registered with the plurality of transmit-receive transducer array, and
      wherein the receive-only transducer array receives and detects thermoacoustically-generated acoustic signals in response to electromagnetic energy delivered into the tissue by the source of electromagnetic energy, and converts the thermoacoustically-generated acoustic signals to thermoacoustic output signals; and
   an imaging assembly connectable to the existing ultrasound imaging system and configured to:
      process the thermoacoustic output signals to generate at least one thermoacoustic image; and
      when connected to the existing ultrasound imaging system, the imaging assembly is configured to:
         receive the ultrasound output signals; and
         process the ultrasound output signals and thermoacoustic output signals to generate at least one composite image.

2. The thermoacoustic imaging system of claim 1, wherein the transmit-receive transducer array comprises a first linear array of transmit-receive array elements, and the plurality of receive-only array elements have a configuration selected from the group consisting of a multiple-linear array on more than one side of the first linear array; a rectangular loop array surrounding the first linear array; and a rectangular dense array surrounding the first linear array.

3. The thermoacoustic imaging system of claim 1, wherein the transmit-receive transducer array comprises a rectangular array of transmit-receive array elements, and the plurality of receive-only array elements have a configuration selected from the group consisting of a multiple-linear array on more than one side of the rectangular linear array; a rectangular loop array surrounding the rectangular array; and a rectangular dense array surrounding the rectangular array.

4. The thermoacoustic imaging system of claim 1, wherein the transmit-receive transducer array comprises a circular array of transmit-receive array elements, and the plurality of receive-only array elements have a configuration selected from the group consisting of a single ring array surrounding the circular array; and a multiple-ring array surrounding the circular array.

5. The thermoacoustic imaging system of claim 1, wherein the at least one composite image includes features of tissue.

6. A thermoacoustic imaging probe for use with an existing ultrasound imaging system for imaging features of tissue, the existing ultrasound imaging system including a transmit-receive transducer array comprising a plurality of transmit-receive array elements that receives and detects echoes from an ultrasound beam delivered into the tissue by the transmit-receive transducer array and that converts the echoes to ultrasound output signals, and an ultrasound imaging probe that houses the transmit-receive transducer array, the thermoacoustic imaging probe comprising:
   a receive-only transducer array including a plurality of receive-only array elements housed in the thermoacoustic imaging probe,
      wherein the receive-only transducer array receives and detects thermoacoustically-generated acoustic signals in response to electromagnetic energy delivered into the tissue by a source of electromagnetic energy, and converts the thermoacoustically-generated acoustic signals to thermoacoustic output signals,
      wherein the thermoacoustic imaging probe, in a form of a sleeve, surrounds and is joined mechanically to the ultrasound imaging probe such that the plurality of receive-only array elements are configured to surround and are in physical alignment and in proximity to the plurality of transmit-receive array elements;
      wherein the plurality of receive-only array elements housed in the thermoacoustic imaging probe are registered with the plurality of transmit-receive array elements housed in the ultrasound imaging probe; and
      wherein the receive-only transducer array communicates the thermoacoustic output signals to an imaging assembly for processing to generate at least one of a thermoacoustic image and a composite image.

7. The thermoacoustic imaging probe of claim 6, wherein the transmit-receive transducer array comprises a first linear array of transmit-receive array elements, and the plurality of receive-only array elements have a configuration selected from the group consisting of a multiple-linear array on more than one side of the first linear array; a rectangular loop array surrounding the first linear array; and a rectangular dense array surrounding the first linear array.

8. The thermoacoustic imaging probe of claim 6, wherein the transmit-receive transducer array comprises a rectangular array of transmit-receive array elements, and the plurality of receive-only array elements have a configuration selected from the group consisting of a multiple-linear array on more than one side of the rectangular linear array; a rectangular loop array surrounding the rectangular array; and a rectangular dense array surrounding the rectangular array.

9. The thermoacoustic imaging system of claim 6, wherein the transmit-receive transducer array comprises a circular array of transmit-receive array elements, and the plurality of receive-only array elements have a configuration selected from the group consisting of a single ring array surrounding the circular array; and a multiple-ring array surrounding the circular array.

10. A thermoacoustic imaging system for use in combination with an existing ultrasound imaging system for imaging features of tissue, the existing ultrasound imaging system comprising a transmit-receive transducer array comprising a plurality of transmit-receive array elements housed within a first ultrasound probe, wherein the transmit-receive transducer array is configured to detect echoes from an ultrasound beam delivered into the tissue by the transmit-receive transducer array, and to convert the echoes to ultrasound output signals, the thermoacoustic imaging system comprising:

an electromagnetic energy source;

a receive-only transducer array comprising a plurality of receive-only array elements housed within a second ultrasound probe, wherein the second ultrasound probe, in a form of a sleeve, surrounds and is joined mechanically to the first ultrasound probe such that the plurality of receive-only array elements are configured to surround and are in physical alignment and in proximity to the plurality of transmit-receive array elements, wherein the plurality of receive-only array elements are registered with the plurality of transmit-receive array elements, and wherein the receive-only transducer array is configured to detect acoustic signals thermally induced in the tissue in response to electromagnetic energy delivered into the tissue by the electromagnetic energy source, and to output thermoacoustic output signals; and an imaging assembly connectable to the existing ultrasound imaging system and configured to:

process the thermoacoustic output signals to generate at least one thermoacoustic image; and when connected to the existing ultrasound imaging system, the imaging assembly is configured to:

receive the ultrasound output signals; and process the ultrasound output signals and thermoacoustic output signals to generate at least one composite image.

11. The thermoacoustic imaging system of claim 10, wherein the transmit-receive transducer array comprises a first linear array of transmit-receive array elements, and the plurality of receive-only array elements have a configuration selected from the group consisting of a multiple-linear array on more than one side of the first linear array; a rectangular loop array surrounding the first linear array; and a rectangular dense array surrounding the first linear array.

12. The thermoacoustic imaging system of claim 10, wherein the transmit-receive transducer array comprises a rectangular array of transmit-receive array elements, and the plurality of receive-only array elements have a configuration selected from the group consisting of a multiple-linear array on more than one side of the rectangular linear array; a rectangular loop array surrounding the rectangular array; and a rectangular dense array surrounding the rectangular array.

13. The thermoacoustic imaging system of claim 10, wherein the transmit-receive transducer array comprises a circular array of transmit-receive array elements, and the plurality of receive-only array elements have a configuration selected from the group consisting of a single ring array surrounding the circular array; and a multiple-ring array surrounding the circular array.

* * * * *